Figure 3A:
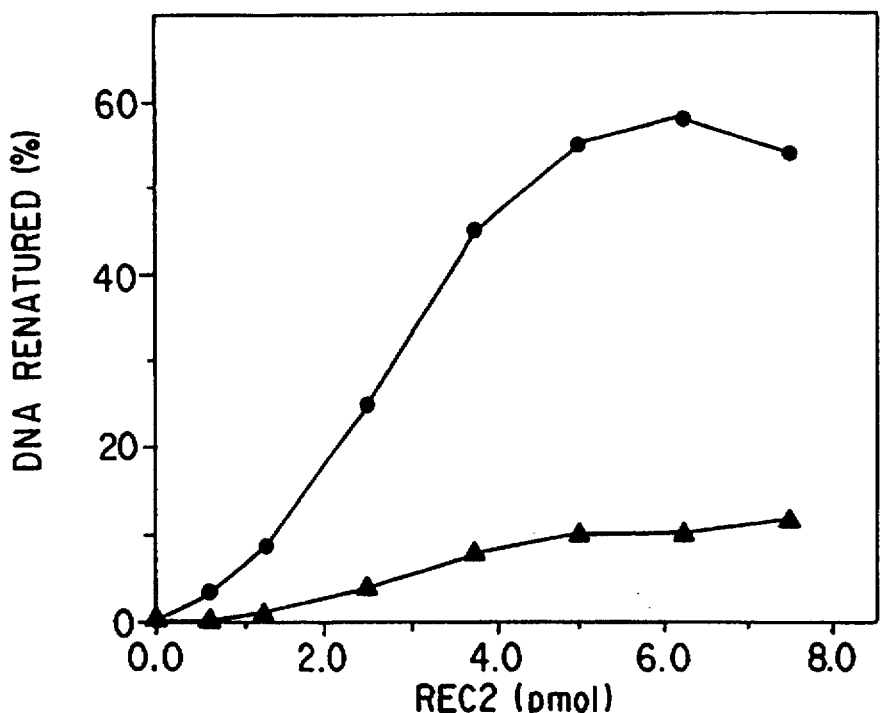

US005780296A

United States Patent [19]
Holloman et al.

[11] Patent Number: 5,780,296
[45] Date of Patent: Jul. 14, 1998

[54] COMPOSITIONS AND METHODS TO PROMOTE HOMOLOGOUS RECOMBINATION IN EUKARYOTIC CELLS AND ORGANISMS

[75] Inventors: William K. Holloman, Yorktown Heights, N.Y.; Eric B. Kmiec, Malvern, Pa.

[73] Assignee: Thomas Jefferson University, Philadelphia, Pa.

[21] Appl. No.: 373,134

[22] Filed: Jan. 17, 1995

[51] Int. Cl.$^6$ ............................................. C12N 15/63
[52] U.S. Cl. ............................ 435/320.1; 536/23.2
[58] Field of Search .................................. 435/320.1

[56] References Cited

U.S. PATENT DOCUMENTS

| 4,873,191 | 10/1989 | Wagner et al. | 435/172.3 |
|---|---|---|---|
| 4,950,599 | 8/1990 | Bertling et al. | 435/172.3 |
| 5,139,941 | 8/1992 | Muzyczka et al. | 435/172.3 |
| 5,354,678 | 10/1994 | Lebkowski et al. | 435/172.3 |

FOREIGN PATENT DOCUMENTS

| 90/09441 | 8/1990 | WIPO . |
|---|---|---|
| 92/07945 | 5/1992 | WIPO . |
| 93/22443 | 11/1993 | WIPO . |
| 94/04032 | 3/1994 | WIPO . |
| 94/08026 | 4/1994 | WIPO . |
| 94/10322 | 5/1994 | WIPO . |

OTHER PUBLICATIONS

Thomas, "Recombination of DNA Molecules", Prog Nuc Acid Res Mol Biol 5;315 (1966).
Holliday et al., "Altered Recombination Frequencies in Radiation Sensitive Strains of Ustilago", Mutation Res 4:275–288 (1967).
Sande et al., "Phosphorylation of N–Protected Deoxyoligonucleotides by T4 Polynucleotide Kinase", Biochem 12;5056–5062 (1973).
Holliday et al., "Genetic Characterization of rec–1, a Mutant of Ustilago maydis Defective in Repair and recombination", Genet Res 27:413–453 (1976).
van Weezenbeek et al., "Nucleotide Sequence of the Filamentous Bacteriophage M13 DNA Genome Comparison with Phage fd", Gene 11:129 (1980).
Doolittle, "Similar Amino Acid Sequences: Chance or Common Ancestry?", Science 241:149 (1981).
Bianchi et al., "Synapsis and the Formation of Paranemic Joints by E. coli RecA Protein ", Cell 34:931 (1983).
Kmiec and Holloman, "Heteroduplex Formation and Polarity During Strand Transfer Promoted by Ustiligo Rec 1 Protein", Cell 33:857–864 (1983).
Bradley et al., "Formation of Germ–line Chimaeras from Embryo–Derived Teratocarcinoma Cell Lines", Nature 309:255–256.
Kmiec and Holloman, "Synapsis Promoted by Ustiligo Rec 1 Protein", Cell 36:593–598 (1984).
Kmiec and Holloman, "Homologous Pairing of DNA Molecules by Ustiligo Rec 1 Protein Is Promoted by Sequences of Z–DNA", Cell 44:545–554 (1986).

Studier and Moffatt, "Use of Bacteriophage T7 RNA Polymerase to Direct Selective High–level Expression of Cloned Genes", J Mol Biol 189:113–130 (1986).
Thomas and Capecchi, "Site–Directed Mutagenesis by Gene Targeting in Mouse Embryo–Derived Stem Cells", Cell 51:503–512 (1987).
Moerschel et al., "Transformation of Yeast with Synthetic Oligonucleotides", PNAS USA 85:524 (1988).
Pearson et al., "Improved Tools for Biological Sequence Comparison", PNAS USA 85:2444–2448 (1988).
Brinster et al., "Targeted Correction of a Major Histocompatibility Class II EαGene by DNA Microinjected into Mouse Eggs", PNAS USA 86:7087–7091 (1989).
Capecchi, "Altering the Genome by Homologous Recombination", Science 244:1288–1292 (1989).
Chisaki and Capecchi, "Regionally Restricted Developmental Defects Results from targeted Disruption of the Mouse Homebox Gene hox–1.5", Nature 350:473–479 (1989).
Ho et al., "Site–directed Mutagenesis by Overlap Extension Using the Polymerase Chain Reaction", Gene 77:51–59 (1989).
Shenoy et al., "Purified Maturation Promoting Factor Phosphorylates pp60$^{c-src}$ at the Sites Phosphorylated during Fibroblast Mitosis", Cell 57:763–774 (1989).
Tsukuda et al., "Isolation of the REC1 Gene Controlling Recombination in *Ustiligo maydis*", Gene 85:335–341 (1989).
Bauchwitz and Holloman, "Isolation of the REC2 Gene Controlling Recombination in *Ustiligo maydis*", Gene 96:285–288 (1990).
Lewin, "Driving the Cell Cycle: M Phase Kinase, Its Partners and Substrates", Cell 61:743–752 (1990).
Pearson, "Rapid and Sensitive Sequence Comparison with FASTP and FASTA", Methods in Enzymology, 183:63–98 (1990).
Fotheringham and Holloman, "Extrachromosomal Recombination Is Deranged in the rec2 Mutant of *ustiligo maydis*", Genetics 129:1053–1060 (1991).
Hunger, "The t(1;19)(q23;p13) Results in Consistent Fusion of E2A and PB1X1 Coding Sequences in Acute Lymphoblastic Leukemias", Blood 77:687–693 (1991).
Reed, "The Role of p34 Kinases in the G1 to S–Phase Transition", Ann Rev Cell Biol 8:529–561 (1992).
Shenoy et al., "Role of p34$^{cdc2}$–mediated Phosphorylations in Two–step Activation of pp60$^{c-src}$During Mitosis", PNAS USA 89:7237–7241 (1992).

(List continued on next page.)

*Primary Examiner*—Eric Grimes
*Attorney, Agent, or Firm*—Daniel Hansburg

[57] ABSTRACT

The invention concerns genes encoding recombinases that can be used to promote homologous recombination in eukaryotic cells and expression vectors that can be used to transiently express recombinases in target cells. One embodiment of the invention encompasses genetically engineered nucleic acids that encode a non-naturally occurring recombinase that causes a greater rate of recombination than does the naturally occurring recombinase. Recombinases from Ustilago maydis, Saccharomyces cerevisiae are specifically included in the invention.

26 Claims, 10 Drawing Sheets

OTHER PUBLICATIONS

Rao and Radding, "Homologous Recognition Promoted by RecA Protein Via non–Watson–Cricks Bonds Between Identical DNA Strands", PNAS USA 90:6646–6650 (1993).

Crystal et al., "Administration of an Adenovirus Containing the Human CFTR cDNA to the Respiratory Tract of Individuals with Cystic Fibrosis", Nature Genetics 8:42–51 (1994).

Kaplitt et al., "Long–term Gene Expression and Phenotypic Correction Using Adeno–Associated Virus Vectors in Mammalian Brain", Nature Genetics 8:148–154 (1994).

Kmiec and Holloman, "ATP Dependent DNA Renaturation and DNA–dependent ATPase Reactions Catalyzed by the *Ustiligo maydis* Homologous Pairing Protein", Eur J Bioch 219:865–875 (1994).

Kmiec and Holloman, "DNA Strand Exchange in the Absence of Homologous Pairing", J Biol Chem 269:10163–10168 (1994).

Pines, "Ubiquitin With Everything", Nature 371:742–743 (1994).

Rubin et al., "Structure of REC2, a Recombinatorial Repair Gene of *Ustilago maydis*, and Its Function in Homologous Recombination between Plasmid and Chromosomal Sequences", Mol Cell Biol 14:6287–6296 (1994).

```
                                                                            AATATTCACGATTCTGATGTGGAAGCGTAAGGAGAAGCAGATTAGGTGTGCTGGTAGGAGCACCTCAACA
-175                                                                                       SSPI
-107  AGCTAGCCGGCCTTGTGTCGTGCTCATCCCAGTCTTCCACAGCCCCAACCATCGTAGGGCTGGCCATGCCCACGATGTTGCGACTCACAGCTTTGCACGTGCTAAATC

1   ATGACTGGCATGCGATGCCGATGCTGGCTGCATTTCGAAACGCATCAAGGGTGCTGTCGTTGTCGAGCAAAGTCTTCAGTACCGACAAGCTCTTCCACCTCCAGCCACCG
  1   M  T  G  I  A  I  A  D  V  G  C  I  S  K  R  I  K  A  C  C  R  R  A  K  L  F  S  T  D  E  I  L  L  S  P  P
                                                NLS

109   CAGCAATTGGCACACGTGTTGCGCATATCCCAAGCAGATGCCGATCTGCTTCTTCTCCAAGTGGCCACGGCATCTGCTCCACCTCCCATCTGGTACTCGATGGCTC
37    Q  Q  L  A  H  V  L  R  I  S  Q  A  D  A  D  L  L  L  L  Q  V  A  T  A  S  A  P  P  P  I  S  V  L  D  A  L

217   AATGGCAAGCTTCCTGCTACCAACCTGGACCAGAACTTCTTTGACGCCGTGCAGCTGCGACGCCGTAAAGATGACGACAATGATGATGACGACGACAAAGCCGATTCC
73    N  G  K  L  P  A  T  N  L  D  Q  N  F  F  D  A  V  A  A  A  D  D  D  D  N  D  D  D  D  K  A  D  S
                                                               CHROMATIN BINDING MOTIF

325   GGTTCGGCCGACGCTTCAGACACGAGCGATGCGGATGATCAAGACCAAGGTTTGCATCGTCTTGCCCCAACACAGGGGTACGATGGCAAC
109   G  S  A  D  A  S  D  T  S  D  A  D  D  Q  H  L  N  D  A  R  F  A  S  S  C  I  V  P  P  T  Q  G  Y  D  G  N

433   TTTCCCGGGCACAATGCTTTGTCTACGATTCGGATGCGGCTCGGAAGCAGTGATGATGCGTAGCATCATCGATGCGGTGATGCACGAAGATATCGAGCTACCGTCCACC
145   F  P  G  A  Q  C  F  V  Y  D  S  D  A  G  S  D  S  D  A  R  S  S  I  D  A  V  M  H  E  D  I  E  L  P  S  T

541   TTTTGCCGTCCACAAACACCACAAACCCACAAACCCACGATGTTGCCCGTGACGAGCATCATGATGGGTATCTTTGCGATCCCAAAGTTGACCACGCCTCGGTCGCCAGAGACGTC
181   F  C  R  P  Q  T  P  Q  T  H  D  V  A  R  D  E  H  H  D  G  Y  L  C  D  P  K  V  D  H  A  S  V  A  R  D  V

649   TTATCGCTCGGACGCCAACGACATGTATTCTTCAAGGCGGCTCGAGAGCTCCCGAGAGCTTGGGGTGCGTTCCGCTGTGCTCCGAGCTCGTCGGTGAA
217   L  S  L  G  R  Q  R  H  V  F  S  S  G  S  R  E  L  D  D  L  L  G  G  G  V  R  S  A  V  L  T  E  L  V  G  E

FIG. 1A
```

```
757  AGGGGCTCTGGTAAGACCCAGATGGCTATCCAAGTTTGCACTTATGCCGCTCTCGGCTTGGTTCCGCTTGAGCCACTTAGGCAACAACACATTT
253  S  G  S  G  K  I  Q  M  A  I  Q  V  C  T  Y  A  A  L  G  L  V  P  L  S  Q  A  D  D  H  D  K  G  N  N  T  F
         MOTIF A
865  CAATCCAGGACTTTCGTACGAGACCCGATACACGCTTCGACCAAAGACGACACACTTAAGGACACTCTGCAGAGACTACGGCATGGAGCCCTCGATTGGATCTCACCGC
289  Q  S  R  T  F  V  R  D  P  I  H  A  S  T  K  D  D  T  L  S  D  I  L  Q  S  Y  G  M  E  P  S  I  G  S  H  R
973  GGTATGGGCGCGTGCTACATCACATCTGGTGGCGAGCGCGCAGGCATTGATGTGAACCAGAGCTCTGGAACTTGCAAGTTTGCTATCAACGAACGCTTTGATCGC
325  G  M  G  A  C  Y  I  T  S  G  G  E  R  A  A  H  S  I  V  N  R  A  L  E  L  A  S  F  A  I  N  E  R  F  D  R
1081 GTCTATCCGGTCTGCGATCCTACACAAAGCTCGCAGGACGCCGATGGGCGCAGGAGGCGAGGCGCGGAGCATTGCTGGCCAAGGCACAGCTTGGTCGTGACAAGGCTTGCCAAC
361  V  Y  P  V  C  D  P  T  Q  S  S  Q  D  A  D  G  R  R  G  A  L  L  A  K  A  Q  Q  L  G  R  R  Q  A  L  A  N
1189 TTGCACATAGCCTGCGTGGCGGATGTCGCTGATGTCGAGGCATTGGAGCATGCTCTCAAGTACAGTCTCCCAGGCTTGATTGTGCGTCGACTGTGGTCGAGTAAGCGTCAGTCAGTCGGGGTA
397  L  H  I  A  C  V  A  D  V  E  A  L  E  H  A  L  K  Y  S  L  P  G  L  I  R  R  L  W  S  S  K  R  Q  S  G  V
1297 TCGCGCGAGATTGGCGTGTGTGGTAGACAATCTTCCAGGCTTTTTCCAGCAGGATGATCAAGGGGACGCAGCAGCAGCCAGTGATATCGACTCGCTCTTCCAACTGCTCTTCCAACGCTCTCAAAGATGCTA
433  S  R  E  I  G  V  V  V  V  D  N  L  P  A  L  F  Q  Q  D  D  Q  A  A  A  S  D  I  D  S  L  F  Q  R  S  K  M  L
                MOTIF B
1405 GTCGAGATGCGGAGATCGCGGATGCGCTCAAGCGCTCAAGGTGCTATCAGTGCTGTACAGTGCTTCAGATTGTGGTTCCTCGCAGGTAGAGCGGTGCTGTGAACCACGTCAGC
469  V  E  I  A  D  A  L  K  R  I  S  A  V  Q  W  R  G  A  S  D  C  G  S  S  A  G  R  A  V  L  V  L  N  H  V  S
1513 GATGCGTTTGGAATCGACAAGCAGATTGCACGGCGCTTCGTATTCGACTCGGCGCACCGGATCCGAACGGTCGGTCTCATTTGCACGCAACGATCCTGGCACATCA
505  D  A  F  G  I  D  K  Q  I  A  R  R  F  V  F  D  S  A  H  R  I  R  T  R  R  S  H  F  A  R  N  D  P  G  T  S
1621 AGTCAAGCGCCAACCTCGGCACTTCAGCGGTGGCACTGGCTCAGCCGTTACCCGACCAGGATCGGCGTTACCCGACCAGCGCGTTACCGACCGACCAAGGATGGCTAGCGATGGATGTGGCTAGCCAGACTGCGTTCACCAGCGGGGCTGCTC
541  S  Q  A  P  T  S  A  F  S  G  G  T  G  S  A  L  P  D  Q  P  P  L  A  M  D  V  A  S  Q  T  A  F  T  S  G  L  L
```

FIG. 1B

```
1729 GCCTCGATCGCCGCCTACGCTGGGCGGAAGCGGTTGGGCGACGCTCGGCTGCCGGTTGCGCTCCGCACACTTGAAGCACGCACTGCACAG
 577  A  S  I  A  P  T  L  A  E  A  V  G  A  R  E  L  D  S  A  C  A  S  N  D  V  P  L  R  T  L  E  A  R  T  A  Q

1837 CTCGGTCAGACCTGGAGCAACCTGATCAATGTGCGCGTGTTTCTGTCCAAAACGCGCCAGGATATGCATGCGCGAGATCAGGCACCAGCATGCGAGCCAGTGCGC
 613  L  G  Q  T  W  S  N  L  I  N  V  R  V  F  L  S  K  T  R  A  R  I  C  M  R  D  D  Q  A  P  A  C  E  P  V  R

1945 CAAAACACCAATCAACGTGGTACGGGAGCAAGTGCTCATGAATACGGTGCGCAAAGCGGTGGTCATCAATCCATTTGGCGCAACCATGTTAGACGTCGGCGTC
 649  Q  N  T  N  Q  R  G  T  A  S  K  S  L  M  N  T  V  R  K  A  A  V  V  I  N  P  F  G  A  T  M  L  D  V  G  V

2053 GACAAGAGCGCGCTGAGACAGCTACGGTTTGTCATTACGCCGCGCAAAGCGGTGCATGTGCTGAATGCGTATCCATCGACAGTGATGCATGCATGGACCGCT
 685  D  K  S  A  L  R  Q  L  R  F  V  I  <u>T  P  R  K</u>  A  V  H  V  L  N  A  Y  P  S  T  V  M  H  A  M  H  A  T  A
                                              CDC 2 KINASE

2161 GACAGGACACGCCCGCTCCAGAGTCACAGAGCAGCAACAGCGCGCGATCAAGAGACCTCTTCGGAGAAGGCGTGCAAGAG
 721  D  S  T  P  A  P  E  S  Q  Q  Q  R  A  A  E  R  H  P  A  E  Q  E  D  A  D  Q  D  L  F  G  E  A  L  Q  E

2269 CATCACTGGCTAGCCATCGACGAGCTCCAATCGCACACCGCCCGGCCTCCCGAGCTCCCGAGCCGCCCAAGCTGGCTGAGTGAAAGATTGACTGAGTCATCTCACGTCT
 757  H  H  W  L  A  I  D  E  L  Q  S  H  T  T  A  R  P  T  S  R  A  A  Q  A  G

2377 GCGATCCAGAATCCTTGTATTTCTACACAGATCACAGGATGTGTTCGTATTCGGCATCATATCGTACACAACTCAAGTTATTGACGTTGAAATGCATTCGTGATTC

2485 ACGCTTGTAGCATGCTAGAGCGGAGGCAAGTCTCTTTGGCGCTCATGTTTAAGCTGGACACGAGAGCGTCGATTCGGGAAAATGGAAAAAGGAAGAACGGCACC

2593 AAGATTGACTGTGTTTAAGTTGAGAGAGCAAATGACAACAGTGAAGCATGCTACAAGTTGTCGAGCTAGGCGCGATCTGCGGTCCCATGATGCTCTCAGCTGCGGTT

2701 CGACGGGCGTTCCAGATGTGCCGACCATGTGTCGTCGCCCACCTGTGCTCGAATTGGTCGAGCGCGGATTTGAACCAGACCTTGACTTGTGCGCCGTGTGGAGGATGTGCT
```

FIG. 1C

2809 TGGTAGCGTCCGATTTGATCGTTTCGCTGGCGGCCAATTTGGTGAAGCCTGCAGCATGGTCTTCGTCGGGCAACAGCAGATCCACGTCTTGCGTCT

2917 GCGTCGCCGAGCTGGGCGTGAGCAGCAACCGCAACAGCGCTGCGAGCAATGTTGGCAACACGCTCACATTCGGCGCTCGACGCATGGCCGATGAATTCACCAACAAGC

3025 TCGCAA

FIG. 1D

```
  1 M T G I A I A D V G C I S K R I K A C C R R A K L F S T D E I L L S P P

37 Q Q L A H V L R I S Q A D A D L L L L Q V A T A S A P P P I S V L D A L

73 N G K L P A T N L D Q N F F D A V A A A D D D D D D N D D D D D K A D S
                                 TRP 1
109 G S A D A S D T S D A D D Q H L N D A R F A S S C I V P P T Q G Y D G N
                                        N-TERM 1
145 F P G A Q C F V Y D S D A G S D S D A R S S I D A V M H E D I E L P S T
                    N-TERM 2
181 F C R P Q T P Q T H D V A R D E H H D G Y L C D P K V D H A S V A R D V

217 L S L G R Q R H V F S S G S R E L D D L L G G G V R S A V L T E L V G E

253 S G S G K T Q M A I Q V C T Y A A L G L V P L S Q A D D H D K G N N T F

289 Q S R T F V R D P I H A S T K D D T L S D I L Q S Y G M E P S I G S H R

325 G M G A C Y I T S G G E R A A H S I V N R A L E L A S F A I N E R F D R
                                      TRP 3
361 V Y P V C D P T Q S S Q D A D G R R D A L L A K A Q Q L G R R Q A L A N

397 L H I A C V A D V E A L E H A L K Y S L P G L I R R L W S S K R Q S G V

433 S R E I G V V V V D N L P A L F Q Q D Q A A A S D I D S L F Q R S K M L

469 V E I A D A L K R I S A V Q W R G A S D C G S S A G R A V L V L N H V S

505 D A F G I D K Q I A R R F V F D S A H R I R T R R S H F A R N D P G T S
                                    TRP 2
541 S Q A P T S A F S G G T G S A L P D Q P L A M D V A S Q T A F T S G L L

577 A S I A P T L A E A V G A R E L D S A C A S N D V P L R T L E A R T A Q

613 L G Q T W S N L I N V R V F L S K T R A R I C M R D D Q A P A C E P V R
                                TRP 4
649 Q N T N Q R G T A S K S L M N T V R K A A V V I N P F G A T M L D V G V

685 D K S A L R Q L R F V I T P R K A V H V L N A Y P S T V M H A M H A T A
                                              TRP 5
721 D S T P A P E S Q Q Q Q R A A E R H P A E Q E D A D Q D L F G E A L Q E

757 H H W L A I D E L Q S H T T A R P T S R A A Q A G
```

FIG. 2

COMPOSITIONS AND METHODS TO PROMOTE HOMOLOGOUS RECOMBINATION IN EUKARYOTIC CELLS AND ORGANISMS

TABLE OF CONTENTS
1. FIELD OF THE INVENTION
2. BACKGROUND TO THE INVENTION
   2.1. THE NEED FOR THE INVENTION AND WORK OF OTHERS
   2.2. THE RECOMBINASE FROM USTILAGO MAYDIS
   2.3. MATURATION PROMOTING FACTOR ($P34^{cdc2}$) AND ITS SUBSTRATES
3. SUMMARY OF THE INVENTION
4. BRIEF DESCRIPTION OF THE FIGURES
5. DETAILED DESCRIPTION OF THE INVENTION
   5.1. REC2 GENES AND METHODS OF CLONING HOMOLOGS OF USTILAGO REC2
   5.2. THE PRODUCTION AND ISOLATION OF REC2 FROM A RECOMBINANT EXPRESSION SYSTEM
   5.3. THE REMOVAL OF THE $P34^{cdc2}$ PHOSPHORYLATION SITE TO AUGMENT RECOMBINASE ACTIVITY
   5.4. THE USE OF REC2-CONTAINING EUKARYOTIC EXPRESSION VECTORS TO PROMOTE HOMOLOGOUS RECOMBINATION OF GENETIC MATERIAL LINKED AND UNLINKED TO THE EXPRESSION VECTOR
      5.4.1. THE CONSTRUCTION OF EXPRESSION VECTORS HAVING PROMOTERS ACTIVE IN MAMMALIAN CELLS
      5.4.2. METHODS OF INTRODUCING THE VECTOR AND THE TARGETED NUCLEIC ACID INTO THE CELL
   5.5. THE USE OF ISOLATED REC2 PROTEIN TO PROMOTE HOMOLOGOUS RECOMBINATION
   5.6. THE USE OF RNA/DNA CHIMERIC OLIGONUCLEOTIDES TO PROMOTE HOMOLOGOUS RECOMBINATION
6. EXAMPLES
   6.1. THE IDENTIFICATION OF USTILAGO RECOMBINASE ACTIVITY AND THE REC2 GENE PRODUCT
   6.2. THE CLONING HUMAN REC2
   6.3. THE PRODUCTION OF RECOMBINANT REC2 FROM USTILAGO
   6.4. THE ACTIVITY OF RECOMBINANT REC2
      6.4.1. MATERIALS AND METHODS
      6.4.2. RESULTS
         6.4.2.1. EXPRESSION OF THE RECOMBINANT REC2 PROTEIN
         6.4.2.2. REANNEALING OF COMPLEMENTARY STRANDS OF DNA
         6.4.2.3. REANNEALING OF A 33-MER TO SINGLE STRANDED, CIRCULAR DNA
         6.4.2.4. SIZE DEPENDENCE OF DUPLEX FORMATION
   6.5. THE USE OF RECOMBINANT REC2 TO PROMOTE HOMOLOGOUS RECOMBINATION
   6.6. THE USE OF REC2 $(T \rightarrow A)^{697}$ EXPRESSION VECTOR TO PROMOTE HOMOLOGOUS RECOMBINATION IN USTILAGO
      6.6.1. CONSTRUCTION OF THE $(T \rightarrow A)^{697}$ EXPRESSION VECTOR
      6.6.2. RESULTS SHOWING THE RATE OF HOMOLOGOUS RECOMBINATION
   6.7. THE CONSTRUCTION OF A REC2 VECTOR FOR EXPRESSION IN MAMMALIAN CELLS This invention was made, in part, with government support under RO1 GM 42482 awarded by the National Institutes of Health. The government has certain rights in the invention.

1. FIELD OF THE INVENTION

The present invention concerns the field of recombinant molecular genetics. Particularly, the invention concerns compounds and methods that can be used to promote genetic recombination between an exogenous polynucleotide and a gene in a eukaryotic organism. More particularly, the invention concerns a class of proteins, termed herein Rec2 proteins, and the genes that encode them. REC2 genes. These proteins are ATPases that catalyze the formation of duplex DNA containing strands that were initially present in two separate duplex DNA molecules (dsDNA) or one dsDNA and one single stranded DNA (ssDNA). The formation of these new duplex DNA molecules, termed homologous pairs, is a necessary whenever genetic homologous recombination between DNA molecules occurs.

2. BACKGROUND TO THE INVENTION

2.1. The Need for the Invention and Work of Others

Those skilled in the art of molecular biology recognize that on frequent occasions it is desired not merely to introduce a new polynucleic acid sequence, i.e. a new gene, into a target eukaryotic cell, but further to place this new gene in a defined location and/or to alter or disable a pre-existing gene in the target cell. In other words, not only is a recombinant cell desired but, it is desired that the genetic recombination be between an exogenous polynucleotide and a pre-defined portion of the target cell genome that is homologous with the exogenous polynucleotide.

A solution to this problem has been offered by Capecchi, M. R., 1989, SCIENCE 244: 1288. In the Capecchi technique, homologous recombination is induced by introducing an exogenous polynucleotide into embryonic stem cells. By suitable construction of the exogenous polynucleotide and choice of the target gene, embryonic stem that have undergone homologous recombination can be selectively expanded and thereafter, reaggregated with normal embryonic cells resulting in viable, chimeric embryos that can develop into fertile adults. The germ line of these founder generation animals contain the recombinant embryonic stem cells. Thus, their offspring includes recombinant animals. By this method, it is possible to construct transgenic animals having particular, pre-defined genetic recombination. Chisaka, O., and Capecchi, M. R. 1991, NATURE 350:473. The same result can be obtained, with considerably more effort, by direct injection of homologous polynucleotides into the pronucleus of an ova. Brinster, R. L. et al., 1989, PROC.NATL.ACAD.SCI 86:7087. See also U.S. Pat. No. 4,873, 191 to T. E. Wagner and P. C. Hoppe. Implementation of both the Capecchi technique and ovum pronuclear injection can be burdensome owing to the low rate of homologous recombination compared to the rate of "illegitimate" recombination, i.e., recombination between non-homologous DNA molecules. For example, in embryonal stem cells illegitimate recombination following introduction of an exogenous polynucleotide appears to be about 1,000 times more prevalent than homologous recombination. Thomas, K. R., and Capecchi, M. R., 1987, CELL 52:503–12.

while Brinster screened approximately 500 transgenic mice to find a single homologous recombinant. To cope these difficulties it may be necessary to isolate many recombinant clones, prepare and analyze by restriction mapping or sequencing genomic DNA from each in order to identify the homologous recombinant of interest or to design complex selection schemes that differentiate between illegitimate and homologous recombinants. For these reasons those skilled in the art appreciate that there is a need for a method to promote homologous recombination in eukaryotic cells.

Attempts have been made to use RecA, a protein that promotes homologous recombination in prokaryotic cells, e.g., *E. coli*, to promote homologous recombination in eukaryotic cells. However, these attempts have not been clearly successful. For example U.S. Pat. No. 4,950,599 to W. Bertling discloses no enhancement in the rate of homologous recombination by use of RecA in eukaryotic cells. Patent publications WO 93/22443 to D. Zarling and E. Sena, and publication 94/04032 to D. C. Gruenert and K. Kunzelmann both purport to correct a genetic defect in a cultured cell line related to cystic fibrosis. These publications disclose primarily experimental data that purport to demonstrate a principle rather than data concerning examples of operative methods. Thus, to allow the exogenous polynucleotide/RecA complexes access to the nucleus, Zarling and Gruenert employ cells that were membrane-permeabilized, although such cells are incapable of further growth. Moreover, even when RecA-promoted homologous recombination was asserted to have taken place in intact cells, these publications provide no quantitative estimates of its frequency. Thus, the use of prokaryotic recA has not been convincingly shown to result in a rate homologous recombination in any viable eukaryotic cell significantly greater than the spontaneous rate of homologous recombination.

2.2. The Recombinase from *Ustilago maydis*

*Ustilago maydis* (hereinafter Ustilago) is a fungus, from which the recombination and DNA repair deficient mutants, rec1 and rec2, have been isolated. Holliday, R., 1967, MUTATION RESEARCH 4:275–288. The rec1 mutant is defective in DNA repair, recombination, growth, and meiosis. Holliday R., et al., 1976, GENET.RES. 27:413–53. The rec2 mutation displays a normal rate of spontaneous mitotic recombination but very low rates of homologous recombination. A diploid homozygous defective rec2 organism cannot complete meiosis (reduction division). Holliday, R., 1967, MUTATION RES. 4:275–88; Fotheringham, S., and Holloman, W. K., 1991, GENETICS 129:1053–60.

An enzymatic activity was isolated from the cytoplasm of Ustilago that promoted the pairing, in the presence of ATP, of single stranded DNA and the homologous linear or supercoiled dsDNA. The same isolate contained an activity that promoted pairing between circular ssDNA and homologous supercoiled DNA and linear dsDNA containing long homologous sequences flanked by long stretches of heterology. Kmiec, E. B., and Holloman, W. K., 1983, CELL 33:857–64; 1984, CELL 36:593–98. Pairing activity was also observed between two duplex circles under conditions where there was either active transcription, a previously formed homologous pairing between dsDNA and ssDNA, i.e., a "D-loop", or the presence of sequences that allowed the formation of the Z-DNA conformation. Kmiec, E. B., and Holloman, W. K., 1986, CELL 44:545–54. The pairing (or recombinase) activity was attributed to a single protein with an apparent molecule weight of 70 Kd on SDS-PAGE, which protein comprised about 85–90% of the protein in the most homogeneous fraction. Kmiec, E. B., and Holloman, W. K., 1994, EUR.J.BIOCH. 219:865–875.

The isolated activity could not be obtained from fractions of rec1 mutant Ustilago. Similarities were noted between the phenotypes of the red mutant and the recA mutant of *E. coli*, and similarities between the above-described activity from Ustilago and the activity of the RecA protein. For these reasons the homologous pairing activity was attributed to a "rec1" protein. However, as will be explained more fully below this attribution is incorrect.

The normal counterpart of the gene effected in the rec1 and rec2 mutations have been isolated from Ustilago genomic libraries. A genome library from wild type Ustilago was constructed in a vector that autonomously replicates in Ustilago. A stock of mutants is transfected with the library and clones that complement the mutant were isolated. The correspondence between the inserts of the isolated clones and the REC1 and REC2 genes were confirmed by showing that each mutant expresses an abnormally sized mRNA, homologous with the identified insert. The REC1 gene was determined by this method to encode an mRNA of about 1.7 kb. Tsukuda, R., et al., 1989, GENE 85:335–41. The REC2 gene was determined to encode an mRNA of about 2.8 kb. The protein it encodes possesses some regions of homology with the bacterial RecA and yeast proteins Dmc1, Rad51 and RAd57. Bauchwitz, R., and Holloman, W. K., 1990, GENE 96:285–288; Rubin, B. P. et al., Sept. 1994, MOL.CELL.BIOL. 14:6287–96.

2.3. Maturation Promoting Factor ($P34^{cdc2}$) and its substrates

The regulation of the growth of eukaryotic cells and particularly the coordination between the replication of a cell's genome (S phase) and the orderly division of that genome into two or four daughter cells (mitosis and meiosis) is accomplished by multiple protein phosphorylations and dephosphorylations catalyzed, respectively, by kineses and phosphatases. The major kinase activity is due to a class of heterodimeric proteins with a common chain, $p34^{cdc2}$, having the enzymatic activity. The second chain of the kinase is a regulatory chain that has been identified as either a cyclin-A or -B-type protein. The substrate specificity of $p34^{cdc2}$ kinase activity is controlled by the associated cyclin. As their name implies, cyclins are unstable proteins the level of which vary throughout the cell cycle. Varying levels of cyclins appear to regulate the beginning not only of mitosis or meiosis but also the onset of S phase. In yeast, there are at least 8 cyclin proteins.

Substrates of $p34^{cdc2}$ include H1 histone, nuclear envelope proteins (lamins), the proto-oncogen pp $60^{src}$, and the transforming protein of the tumor virus SV40. Reviewed Lewin, B., 1990, CELL 61:743–52; Reed, S. I., 1992, ANN.REV.CELL BIOL. 8:529–61; Pines, J., 1994 NATURE 371:742. The different substrate proteins $p34^{cdc2}$ kinase are phosphorylated at different phases of the cell cycle. When the target of $p34^{cdc2}$ phosphorylation has an identified enzymatic function, e.g., $pp60^{src}$, phosphorylation is associated with activation of the target protein's enzyme activity, though the phosphorylation does not necessarily directly cause activation of enzyme function. Shenoy, S., et al., 1992, PROC.NATL.ACAD.SCI. 89:7237–41.

The consensus phosphorylation site of $p34^{cdc2}$ kinase action is the sequence (Ser or Thr)-Pro-any amino acid-(Arg or Lys)SEQ ID NO:15-, the Ser/Thr being phosphorylated. Shenoy, S., et al., 1989, CELL 57:763–74 While it is clear that the replacement of the Ser/Thr in the consensus site by any other amino acid would block the action of $p34^{cdc2}$ kinase, and hence, block its regulation of the activity of the mutant protein (mutein), it is, in general, unpredictable whether such a mutein would be supra-active or inactive.

3. SUMMARY OF THE INVENTION

The present invention comprises: a genus of proteins, collectively termed Rec2, a species of which is found in every eukaryote: super-active muteins of those proteins; vectors suitable for the expression of both the naturally occurring and mutant proteins in prokaryotes and eukaryotes and methods of recovering the protein in active form; and methods of using isolated Rec2 protein and REC2-containing expression vectors to promote homologous recombination in eukaryotic cells. The application discloses the novel REC2 genes of mouse, human and yeast.

The invention is useful to promote homologous recombination in cultured cells for such purpose of: making specific genetic alterations in cells used to produce a recombinant protein; introducing specific alterations in embryonic stem cells or ova (gametes) to be used in the construction of transgenic animals; modifying in vitro explanted tissue stem cells, e.g., hematopoietic stem cells, which can then be continued in culture, or reimplanted into a non-human host, to produce a specific product, or reimplanted into a human subject in need of gene therapy for a medical condition amendable thereto. The methods and compounds of the invention can also be employed to promote homologous recombination within an animal including a human.

5 4. BRIEF DESCRIPTION OF THE FIGURES

FIG. 1. The nucleic acid sequence of Ustilago REC2 with annotated derived amino acid sequence (Dayhoff code).

FIG. 2. The composite amino acid sequence of Ustilago REC2 derived from direct Edman degradation of the isolated protein and by inference from the nucleic acid sequence.

Figure 3B:
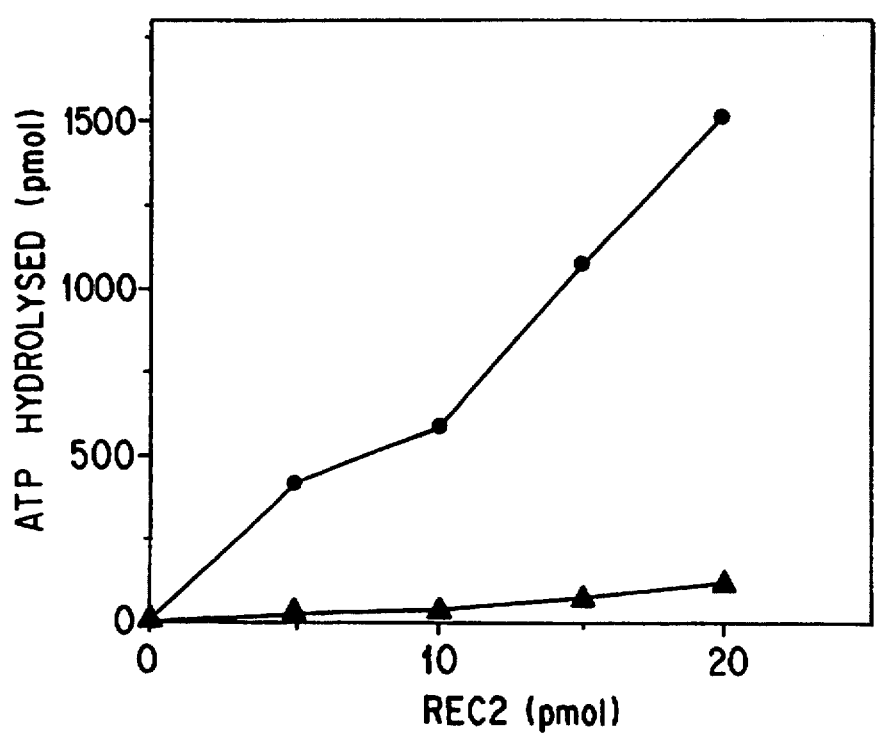
Figure 4A:
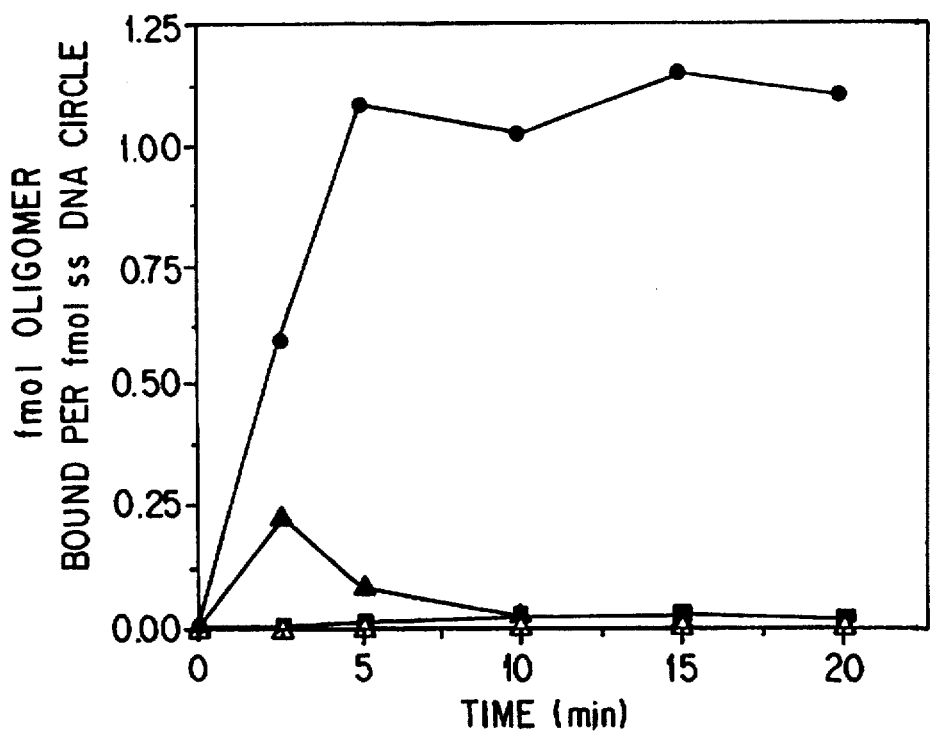
Figure 4B:
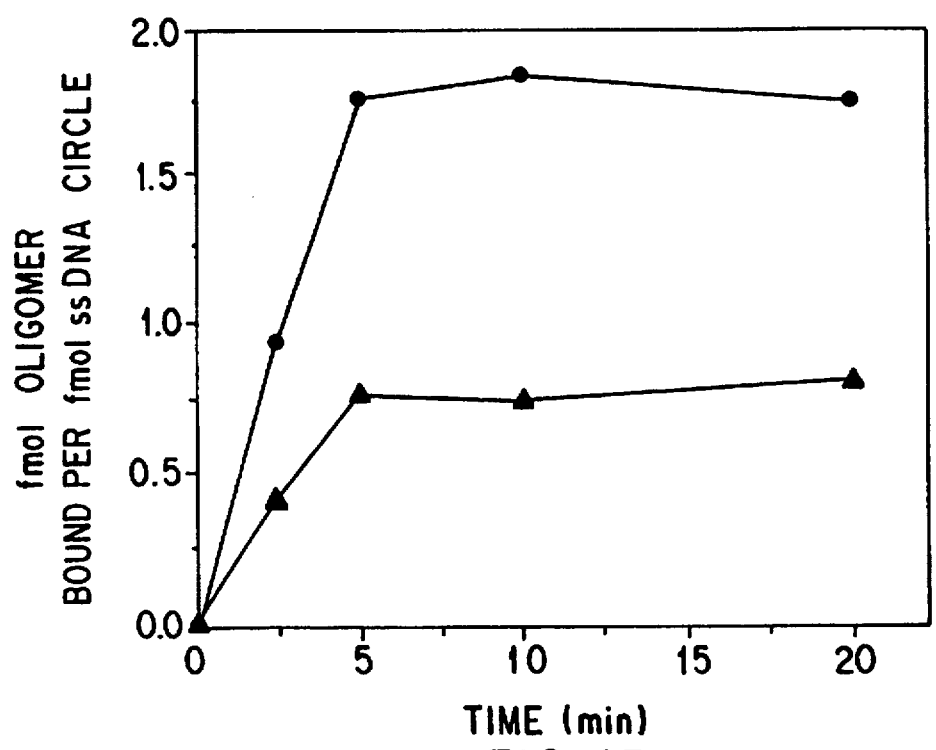

FIGS. 3A and 3B. DNA renaturation and ATPase activities of recombinant REC2 protein. FIG. 3A: 20 μM denatured P22 [$^3$H]DNA (as nucleotide) either in the presence of 1 mM ATP (circles) or with no ATP (triangles); FIG. 3B: in the presence (dots) or absence (triangles) of 20 μM M13 DNA. FIGS. 4A and 4B. Complementary and identical strand pairing by recombinant REC2 with circular single stranded M13. FIG. 4A: Identical strand pairing to a 33-mer identical with M13. In the absence of M13 single-stranded DNA the background of $^{32}$p label retained was usually 5% of the input labeled oligonucleotide. Results are corrected for this background. (closed circles) complete reaction; (closed triangles) øX174 DNA in place of M13 DNA; (closed squares) complete reaction plus 5 mM ADP; (open triangles) complete reaction minus ATP; (open circles) complete reaction treated with 100 μg/ml proteinase K for 10 min. FIG. 4B: Complementary strand pairing to a 44-mer. (closed circles), complete reaction; (closed triangles), complete reaction treated with proteinase K for 10 min.

Figure 5A:
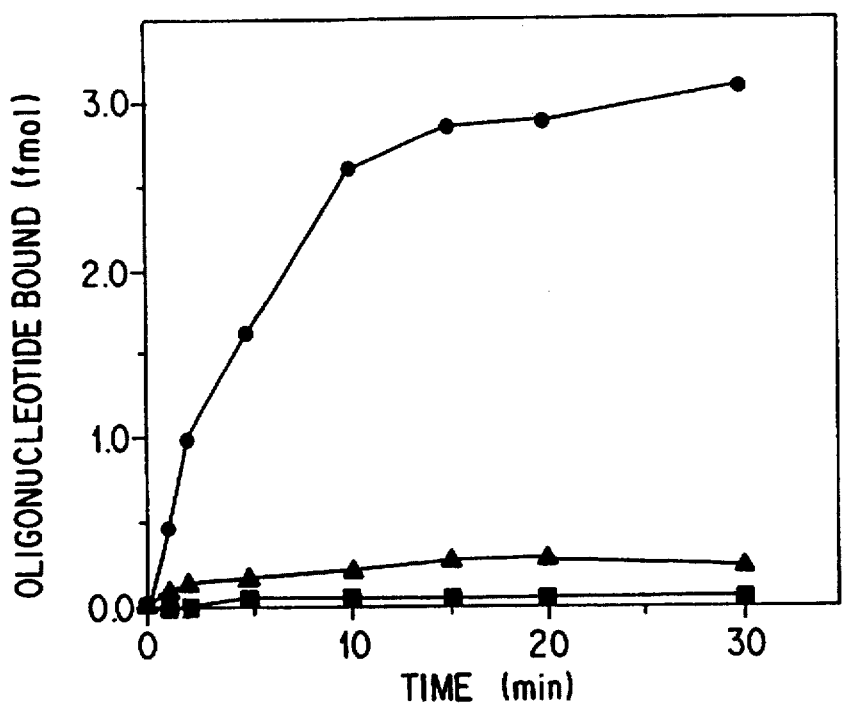
Figure 5B:
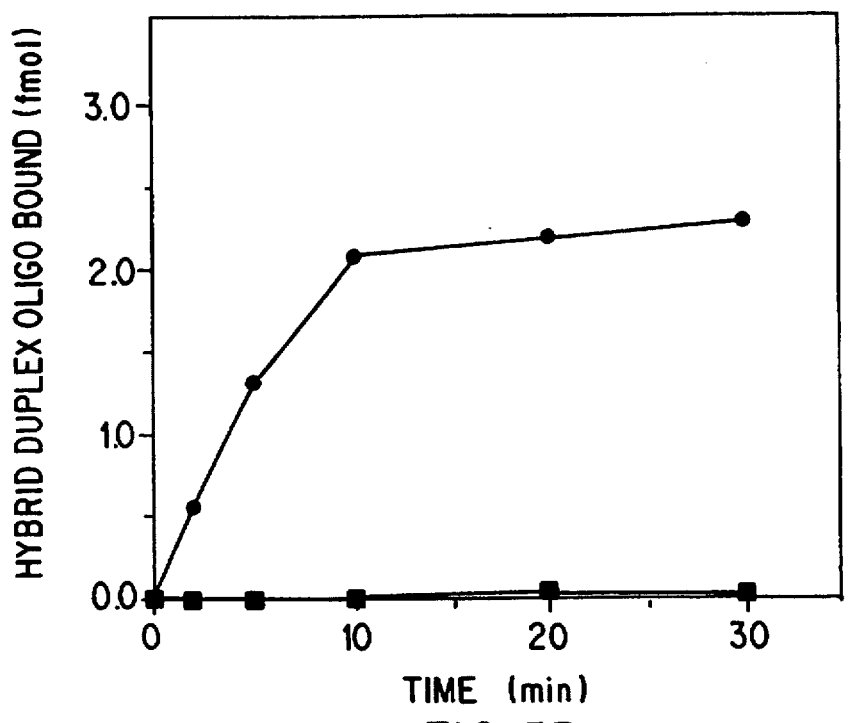

FIGS. 5A and 5B. Threshold length dependence for pairing with DNA/DNA and DNA/RNA hybrids. FIG. 5A DNA/DNA hybrids; (circles) 72-mer; (triangles) 50-mer; (squares) 30-mer.

FIG. 5B: RNA/DNA hybrids using 30-mer duplexes. DNA/RNA hybrid (circles); DNA/DNA hybrid (squares); (triangles) RNA/DNA hybrid in reaction with Ml3mp18 single-stranded RNA.

Figure 6:
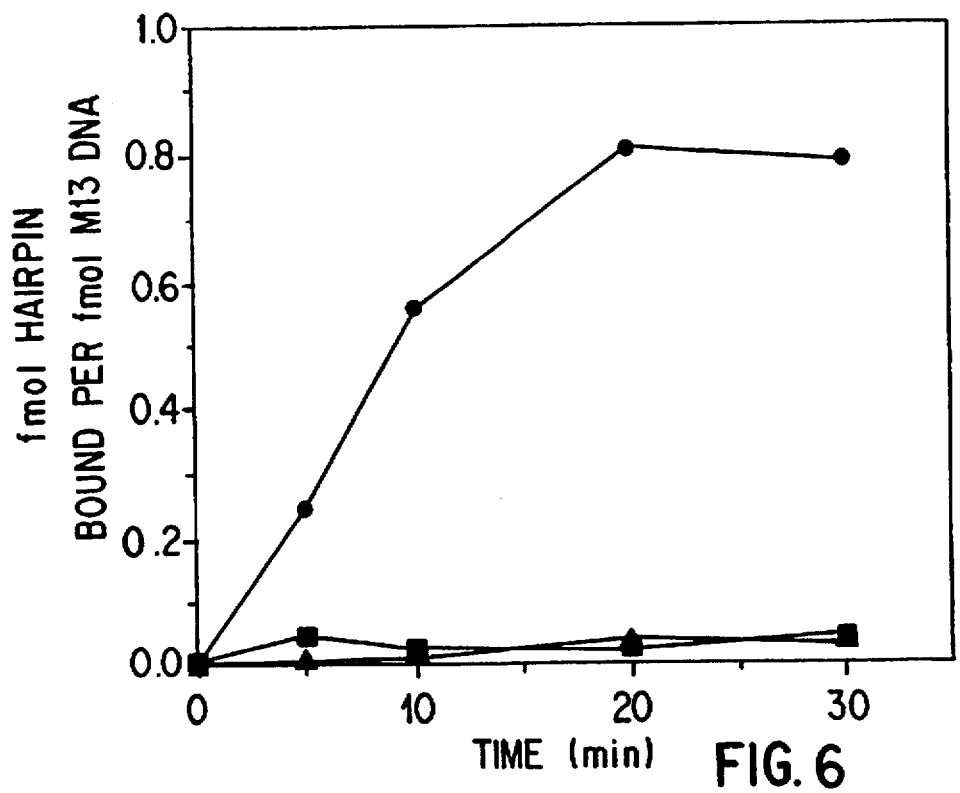

FIG. 6. Homologous pairing with an RNA/DNA oligonucleotide hairpin. (circles) RNA/DNA chimeric hairpin with M13mp19 DNA; (triangles) RNA/DNA chimeric hairpin with M13mp18 DNA; (squares) DNA hairpin with M13mp19 DNA.

Figure 7:
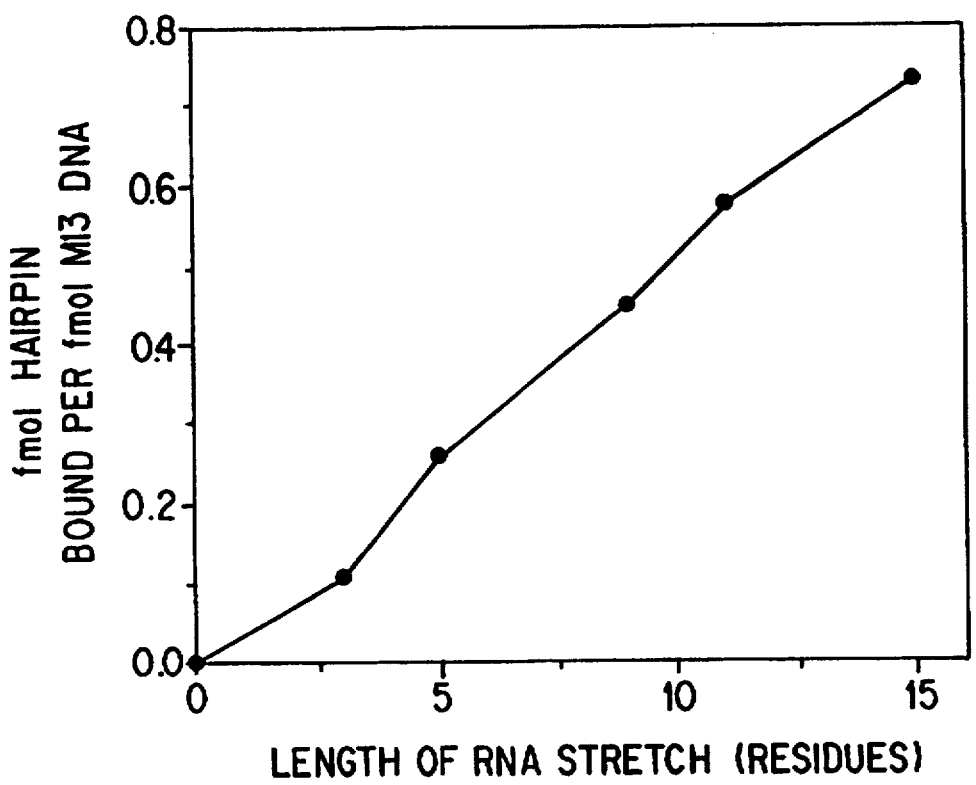

FIG. 7. Contribution of RNA to homologous pairing of chimeric hairpin duplexes. Hairpin forming chimeric RNA-DNA oligonucleotide 44-mers were synthesized such that the RNA length was progressively reduced by replacement with DNA residues. The total base-pair-forming length along both strands was kept at 18 residues.

Figure 8:
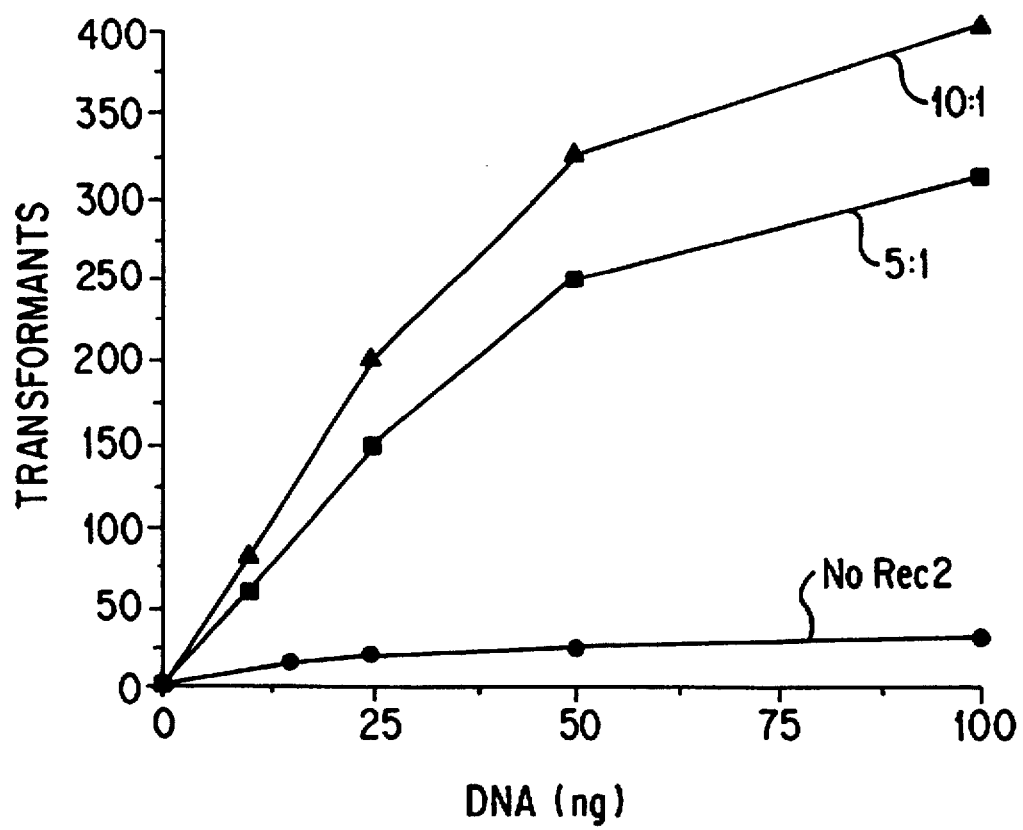

FIG. 8. Transformation of Saccharomyces strain B7528 by homologous recombination of a 50-mer ssDNA oligomer containing a one base insertion. (-X-), 10:1 mol recombinant Rec2:mol oligomer; (-■-), 5:1.

5. DETAILED DESCRIPTION OF THE INVENTION

The present invention is based, in part, upon the unexpected result that the gene that encodes the Ustilago homologous pairing (recombinase) activity is encoded by the REC2 gene. The protein associated with the isolated recombinase activity described hereinabove, was a truncated form of Ustilago Rec2. Based on the identification of REC2 as encoding a homologous pairing (recombinase) enzyme, genes encoding the recombinases of yeast, mice and humans have been identified.

The present application teaches that Rec2 contains a single p34$^{cdc2}$ kinase phosphorylation site that includes Thr$^{697}$. The invention is further based, in part, on the unexpected discovery that the mutein of Rec2, in which the wild-type Thr$^{697}$ residue is replaced by an aliphatic residue (T→A$^{697}$), hereinafter Rec2$^{super}$, causes supra-normal rates of homologous recombination when expressed in wild-type Ustilago. The invention encompasses Rec2 and Rec2$^{super}$ proteins and REC2$^{super}$ genes from Ustilago. The application discloses methods of cloning homologs of REC2 from other species and specifically encompasses the REC2 homologs of Saccharomyces cerevisiae.

The invention also encompasses methods of using expression vectors to introduce, into a target cell of interest, wild-type and T→A$^{697}$ REC2 genes as well as methods of using purified Rec2 and Rec2$^{super}$ proteins to augment the rate of homologous recombination. The invention further encompasses the use of mixed polydeoxyribo/ribonucleic acids, as exogenous polynucleotide substrates for Rec2 recombinases.

The purpose of the present invention is to provide a method whereby preselected genes in a target cell can be altered. A gene in a target cell is altered by homologous recombination with an exogenous polynucleotide, that contains a region that differs from the target gene. Hereinafter, when references are made to an exogenous polynucleotide, exogenous nucleic acid or exogenous ssDNA, that is homologous with a target gene, it is to be understood, without explicit recitation, that a portion of the sequence of the exogenous polynucleotide, etc., is homologous with a portion of the target gene and that interposed between the portions homologous to the gene is a heterologous portion so that homologous recombination between the polynucleotide and the target gene effects an alteration its sequence.

The types of cells in which genetic modifications can be made using the invention include all eukaryotic cells. In one embodiment, the cells are yeast or fungal cells such as Saccharomyces cerevisiae or Ustilago maydis. In alternative embodiments, cells of higher eukaryotes can be used, such as: human tissue-specific stem cells and precursor cells, including hematopoietic stem and precursor cells; ova cells that are suitable for the preparation of transgenic animals such as transgenic mice, rats, swine and cattle; and embryonal stem cell lines such as CC1.2. See Bradley, A., et al., 1984, NATURE 309:255–56. In addition to the ex vivo embodiments, the invention can be advantageously employed in vivo to promote homologous recombination in any cell type into which exogenous DNA can be introduced and expressed.

The invention can be employed to promote homologous recombination in cell types that are not proliferating, such as, for example, liver cells and neuronal cells of the central and peripheral nervous system. The invention can also be used to promote homologous recombination in cell types that are actively proliferating such as the mucosal cells of the gut and respiratory system.

The present invention can, in a further embodiment, be employed to target specific genes that arise by the translocation of genetic elements, such as occurs normally in lymphoid cells and, pathologically, in many types of neoplasms. Because such translocations create DNA sequences, not found in other cells, homologous recombination occurs only within the specific cell lineage containing the translocation. According to the inventor, the exogenous nucleic acid can be constructed to introduce a sequence that would lead to the disruption of the expression of the unique sequence, such as, by way of example, a splice donor or splice acceptor site or, if the unique sequence is located close to an exon of the gene, the exogenous nucleic acid can be used to introduce a frame shift mutation or stop codon, disrupting expression of the translocated gene.

5.1. REC2 Genes and Methods of Cloning Homologs of Ustilago REC2

Genes that are homologous with Ustilago REC2 can be cloned from any eukaryotic species by screening genomic libraries or cDNA libraries of mitotically and/or meiotically active tissue, e.g., from testicular libraries or from other rapidly dividing cells, from the species by a variety of techniques. The libraries can be screened by hybridization with a probe that consists of the entire REC2 gene or fragments thereof.

Genome blots of Saccharomyces, a genus of the type Ascomycepes yeast form fungi, which type excludes Ustilago strongly and specifically hybridizing bands. This result indicates that the REC2 genes of any species of the Ascomycepes group can be cloned directly from a genome library or by band cloning of a genomic digest.

Alternative methods to isolate putative REC2 genes from other species of eukaryotes utilize the paired sense and antisense oligonucleotides, the sequences of which encode, or are complementary to nucleic acids encoding, the portions of Rec2 that are highly conserved among species. One such portion consists of residues 226–270, which shows homology with S. cerevisiae proteins Dmc1, Rad57 and Rad51 and with the E. coli protein RecA. The oligonucleotides are selected to bracket portions of the gene of about 100 to 500 bp. The paired oligonucleotides can be used as primers in a polymerase chain reaction (PCR) to amplify the bracketed fragment of the gene. The amplification products may then be cloned, sequenced and those, the sequence of which indicates that they are fragments of a Rec2 gene, can be used as probes to isolate the entire gene from a suitable library.

The identity of a clone that hybridizes with a Ustilago REC2 probe (hereinafter a "putative REC2 gene") can be determined by expressing the gene in a prokaryotic expression system, isolating and assaying the product according to the methods set forth hereinafter. The finding of any of the activities of promoting complementary or identical strand pairings, or homologous recombination confirms that the putative gene is a REC2 gene. Alternatively, the putative gene can be sequenced and the sequence compared by use of any of the sequence comparison algorithms known in the field. The FASTA algorithm of Pearson is suitable. Pearson, W., 1990, METHODS IN ENZYMOLOGY, 183:63 (Academic Press, San Diego, CA; Pearson, W. et alia, 1988, PROC.NAT-L.ACAD.SCI 85:2444.

Procedures for the comparison of the sequences of putative Rec2 proteins from species other than Ustilago with the sequence of Ustilago Rec2 are well known to those skilled in the field. The procedure to calculate a "normalized alignment score" is described by R. F. Doolittle, 1981, Science 241:149 (see particularly pages 154–155), which is hereby incorporated by reference in its entirety. A putative REC2 gene having a normalized alignment score, when compared with Ustilago Rec2, of greater than 150 and having an A motif and a B motif as indicated in FIG. 1, can be tested to determine whether it is a recombinase. Useful tests of a potential recombinase include genetic complementation tests to determine whether the putative gene complements the defects in the REC2-1 gene of Ustilago and biochemical tests of the protein product of the putative REC2 gene that test whether the protein is an ATPase and catalyzes the formation of complementary or identical strand pairings of polydeoxynucleic acids.

A putative REC2 gene having a normalized alignment score of about 200 or greater when compared with the entire sequence of Ustilago Rec2 can be considered a homolog of REC2 gene.

5.2. The Production and Isolation of REC2 from a Recombinant Expression System According to the present invention a Rec2 protein can be produced from any full length REC2 gene or cDNA. In the first step of the process to produce Rec2 protein, the sequence surrounding the initiation codon of REC2 is modified by insertion of a restriction site, e.g., a NdeI site (5'-CA/TATG-3'). Such a modification can be accomplished by PCR using a near homologous primer. Using this restriction site the amplified REC2 gene can be inserted into an expression vector immediately 3' to a hexahistidine encoding sequence. The pET expression system vector (Novagen, Inc., Madison, Wis.) or equivalent are suitable. Expression systems wherein the REC2 gene is operably linked to the polyhedrin promoter of the baculovirus Autographica californica virus which is then grown in insect cells from the fall armyworm, Spodoptera frugiperda, are also suitable for the expression of the Rec2 protein.

When expressed in E. coli the Rec2 protein can be recovered as an active recombinase by the following procedure. After induction of Rec2 protein production, the bacterial cells are harvested, sonicated and the soluble supernatant (15,000 rpm×20 min, Sorvall SS34) discarded. The pellet is then solubilized in a high NaCl (about 0.2–1.0M), mildly alkaline (ph 7.9) buffer containing a chaotropic denaturing agent, e.g., 8M urea, 6M guanidine HCl or the like. The material that remains insoluble after exposure to the chaotropic buffer is discarded and the solubilized material is passed over a nitrilotriacetic acid agarose column that had been loaded with $Ni^{++}$ (NTA-agarose) (Qiagen, Chatsworth Calif.) or its equivalent. When expressed in a baculovirus system the protein can be solubilized by any method and passed over that NTA-agarose column so that the recombinant Rec2 protein is bound.

The material specifically bound to the NTA-agarose is eluted by high imidazole, recovered and dialyzed into a moderately alkaline Tris buffer (pH 8.5) saline (0.05–0.2M NaCl) buffer (TNE buffer) containing 6M urea or similar chaotropic agent for at least 1 hour and preferably at least 3 hours. The chaotropic agent is then slowly diluted by dialysis against an increasing volume of TNE without chaotropic agent. The initial dialysis is performed with a dialyzing volume equal to the dialysate (sample) volume; the dialyzing volume is slowly increased, at a uniform linear rate, until a final volume of 20× the initial dialysate is reached over a period of at least 5 hours. Recombinant Ustilago Rec2, so prepared has an apparent molecular weight of 110 Kd, when electrophoresed on SDS-PAGE, and an actual molecular weight of 84 KD.

The recombinant Rec2 protein of any eukaryotic species, so prepared, is suitable for use in the invention. In the presence of ATP, a Rec2 protein will cause the pairing and transfer of the ssDNA accompanied by the hydrolysis of the ATP. Thus, the activity of the recombinant protein may be assessed by assaying the formation of complexes between homologous linear dsDNA and circular ssDNA or by assaying its ATPase activity. Either dsDNA or ssDNA acts as a cofactor for the ATPase activity. Quantitatively, the ATPase activity of the Rec2 of the present invention is greater than 4 moles ATP/min per mole of protein and usually between about 5–400 mole ATP/min per mole of protein when 50 µM M13mp18 ssDNA are present and the other assay conditions are 25 mM Tris pH 7.5, 10 mM $MgCl_2$, 1 mM DTT and 0.5 mM $|\alpha-P^{32}|$ ATP. Kmiec, E. B., and Holloman, W. K., 1994, EUR.J.BIOCH. 219:865–875. Those skilled in the art appreciate that protein prepared according to the present invention can contain a substantial fraction of denatured and, hence, enzymatically inactive protein. The above-described specific activities refer to the activity of the aggregate product not to the specific activity of the active component within the product.

5.3. The Removal of the $p34^{cdc2}$ Phosphorylation Site to Augment Recombinase Activity The REC2 genes of the invention contain $p34^{cdc2}$ kinase consensus phosphorylation site, which is a tetrapeptide (Ser/Thr)-Pro-Xxx-(Arg/Lys)-, wherein the residues in parentheses are alternatives at a position and "Xxx" indicates any amino acid may be present. Ustilago Rec2 contains a $p34^{cdc2}$ kinase consensus phosphorylation site which begins at $Thr^{697}$, the phosphorylated amino acid. To prevent the potential regulation by $p34^{cdc2}$ of the action of Rec2, $Thr^{697}$ can replaced by any amino acid except Ser; replacement by an amino acid such as glycine or alanine is preferred. Site directed mutagenesis may be conducted by any method. The method of Ho, S. N., et al., GENE 77:51–59 (herewith incorporated by reference in its entirety), is suitable. According to the method of Ho, overlapping, mutated genome fragments are synthesized in two separate PCR reactions. Of the four primers are used in the two reactions, two are complementary to each other and introduce the desired mutation. The PCR reactions are performed so that the 3' end of the sense strand of one product is complementary to the 3' end of antisense strand of the other. The two PCR products are denatured, mixed and reannealed. The overlapping partial duplex molecules are then extended form a full length dsDNA, amplified in a third PCR reaction, the product isolated and inserted by conventional recombinant techniques into the parent gene.

Unexpectedly, the replacement of $Thr^{697}$ by Ala results in a Rec2 (hereinafter $Rec2^{super}$) that is 8–10 fold more active in Ustilago than the wild type Rec2. Further, while the introduction of multiple copies of REC2 into Ustilago does not result in increased homologous recombination, except in $REC2^-$ deficient organisms, the introduction of a $REC2^{super}$ expression vector results in an 8–10 fold increase rate of homologous recombinants even in wild-type Ustilago. The advantages of using a $REC2^{super}$ expression vector depend upon the physiological state of the $p34^{cdc2}$ site in the cell-type of interest. The practitioner's choice between the use of Rec 2 and $Rec2^{super}$ proteins or expression vectors, thus, depends upon the cell-type to be transfected and the practitioner should investigate which is appropriate for her intended use.

5.4. The Use of REC2-containing Eukaryotic Expression Vectors to Promote Homologous Recombination of Genetic Material Linked and Unlinked to the Expression Vector In one embodiment of the invention homologous recombination between a targeted gene of a cell and an exogenous nucleic acid homologous with the targeted gene is effected by simultaneously introducing a vector that expresses Rec2 or $Rec2^{super}$ and the exogenous nucleic acid. The exogenous nucleic acid and the REC2 gene can be present on the same molecule (linked) or can be present as separate molecules. The optimum concentration of REC2 expression vector and, when the expression vector and the exogenous nucleotide are unlinked, the ratio between vector and exogenous nucleic acid can be determined by targeting a selectable target gene in the cell of interest and determining the optimal amount and ratio for that gene. The optimal amount of expression vector and the ratio of expression vector to exogenous nucleic acid is a function of the cell type and the size of the exogenous nucleic acid.

5.4.1. The Comstruction of Expression Vectors Having Promoters Active in Mammalian Cells The REC2 gene of the invention can be expressed in a mammalian cell by any expression system that places a REC2 gene in operable linkage with a promoter which is active in the mammalian cell. As used herein a promoter includes both the initial binding site of the RNA polymerase, which is alternatively termed a TATA box or a Goldberg-Hogness box, and the upstream promoter elements, which frequently contain the sequences CAAT or CACC. Promoters suitable for the expression of REC2 in mammalian cells include promoters obtained from mammalian viruses such as Cytomegalovirus, SV40 and Moloney Leukemia Virus. Further augmentation of the transcription level of REC2 genes can be obtained by use of enhancer sequences.

5.4.2. Methods of Introducing the Vector and the Targeted Nucleic Acid into the Cell Any method that is suitable for introducing nucleic acid into a cell may be used. Such methods include by way of example electroporation, liposomal delivery, calcium phosphate precipitation, Replication defective viral particles, such as: adeno-associated virus, see, e.g., U.S. Pat. No. 5,354,678 to Lebkowski and No. 5,139,941 to Muzcyzka; adenovirus, see, e.g., WO 94/08026 to Kahn, A. and others, and WO 94/10322 to Herz, J.; or herpes amplicon vectors see, e.g., WO 90/09441 and WO 92/07945 to Geller, A. I., can also be used to introduce a REC2 gene and a linked exogenous nucleic acid. Scientific publications concerning adenovirus and adeno-associated virus can be found at Crystal, R. G., et al., 1994, NATURE GENETICS 8:42; and Kaplitt, M. G. et al., 1994, NATURE GENETICE 8:148, respectively.

5.5. The Use of Isolated REC2 Protein to Promote Homologous Recombination

In an embodiment of the present invention, Rec2 protein can be used to promote recombination between a target gene and an exogenous ssDNA molecule that is homologous with a portion of the gene. The length of the DNA molecule can be between about 25 nt and 1 kb. In a preferred embodiment the there are between about 10 nt and about 40 nt of homologous sequence flanking a non-homologous portion of the exogenous ssDNA. The non-homologous portion can be between 1 nt and 1 kb. In a preferred embodiment the ssDNA is about 50 nt in length and the non-homologous portion is 1 nt in length. A mixture of Rec2 protein to exogenous ssDNA having a molar ratio of between 1:1 and 50:1 can be used for the practice of the invention, a mixture of 5:1 to about 10:1 is preferred for the practice of the invention when the exogenous ssDNA is about 50 nt in length. Proportionately more Rec2 can be used when the exogenous ssDNA is longer.

Recombinant Rec2 is prepared according to the invention. A complex of ssDNA and Rec2 is preformed in a small volume. For example, a mixture at ssDNA (50 nt) at about 20 ng/μl and a 10× excess of Rec2 will form complexes suitable for the practice of the invention when incubated about 10 minutes at 31° C. in a solvent of 2 mM Tris (pH 7.5). Proportionately longer incubations can be employed if the concentration of Rec2 is reduced.

The complex can be introduced by any means effective to introduce protein/DNA complexes into the cell type of interest, so long as the method does not cause the denaturation of the Rec2. In one embodiment the Rec2/ssDNA complex can be introduced by electroporation. To facilitate electroporation the Rec2 protein can be dialyzed into low ionic strength buffer prior (e.g., 2 mM Tris pH 7.50 or distilled water) prior to the formation of the Rec2/ssDNA complexes.

5.6. The Use of RNA/DNA Chimeric Oligonucleotides to Promote Homologous Recombination In an alternative embodiment of the invention the exogenous polynucleotide can be a mixed nucleic acid containing ribonucleotides and deoxyribonucleotides, the two strands of which are covalently linked by a single stranded tetranucleotide, hereinafter a "hair-pin" linkage. Small self-complementary, hair-pin linked, polydeoxynucleotides, having a duplex sequence length of about 15–20 bp do not participate in homologous recombination. Their inactivity is not due to the presence of the hairpin sequence linking the strands. However, if, in one strand of the duplex, the deoxynucleotides are replaced by ribonucleotides to produce a self-complementary "chimeric-polynucleotide" the resultant molecule (hereinafter "mono-chimeric exogenous polynucleotide") can be a substrate in the homologous recombination process. This invention is disclosed in commonly assigned, copending U.S. patent application Ser. No. 08/164,303, which is incorporated herein by reference in its entirety. Further embodiments of the invention are disclosed in U.S. patent application Ser. No. 08/353,651, filed Dec. 9, 1994, by Eric B. Kmiec, entitled: "COMPOUNDS AND METHODS FOR SITE DIRECTED MUTATIONS IN EUKARYOTIC CELLS," which is hereby incorporated by reference in its entirety. In these latter embodiments a non-homologous nucleic acid is interposed between two chimeric polynucleotides, the ends of which are hair-pin linked together so as to form a single closed-end substantially self-complementary linear duplex nucleic acid having two distinct regions of RNA/DNA chimerism. Such molecules are hereinafter termed "di-chimeric exogenous nucleic acids". The size of the non-homologous DNA insert can be up to about 1 kb. The resultant molecule consisting of two chimeric-polynucleotide regions of about 20–50 bp in length separated by a DNA insert of up to about 1 kb.

In an embodiment of the present invention an expression vector suitable for Rec2 production is introduced into the target cell accompanied by the either mono-chimeric or di-chimeric nucleic acids. The ratio of expression vector to exogenous chimeric nucleic acid to be used is between 1:1 and 1:10$^4$. In an alternative embodiment complexes between a Rec2 protein and the chimeric exogenous nucleic acids are pre-formed, according to the teaching of Sect. 5.5 supra.

6. EXAMPLES

6.1. The Identification of Ustilago Recombinase Activity and the REC2 Gene Product The REC2 gene was cloned by complementation of the rec2-1 mutant. A Ustilago genome library was made using a vector that autonomously replicates in Ustilago. Bauchwitz, R., and Holloman, W. K., 1990, GENE 91:285. This DNA sequence and the deduced protein sequence is given in FIG. 1. See also Rubin, B. P., et al., September 1994, MOL.CELL.BIOL. 14:6287–96.

The identification of the Rec2 gene product and the recombinase activity isolated from Ustilago was made as follows. The major protein species in the most homogeneous Ustilago fractions having recombinase activity was subjected to Edman degradation sequencing. In addition, this protein was subjected to tryptic proteolysis and 5 major peptides isolated. Edman degradation sequencing of these peptides was then performed. In FIG. 2 the same protein sequence as FIG. 1 is presented and, additionally, in bold large capital letters, are shown the sequences which were obtained by Edman degradation of the protein from the recombinase active fractions. There are 5 sequences from the tryptic peptides, between 6 and 9 residues in length, and the two "N-terminal" sequences, 9 and 10 residues respectively. These sequences clearly established that the REC2 gene encodes the major protein in the Ustilago recombinase isolate. The "N-terminal" sequence data further indicate that the protein present in the Ustilago recombinase isolate was not native Rec2, but was a mixture of two different truncated proteins lacking the N-terminal 129 residues or 153 residues, respectively.

Cells having a rec2 mutation were transfected, a wild-type revertant isolated and the episome insert encoding the presumptive Rec2 protein cloned and sequenced.

The activity of the Ustilago recombinase isolate had been detected only in vitro experiments using isolated components, not in assays involving living cells. The protein in the active isolate lacked both the nuclear localization sequence (NLS), residues 14–17, and the Chromatin Binding Motif (CBM), residues 93–103, regions which are predicted to be necessary for normal function of a eukaryotic recombinase. This prediction is supported by the observation that although extracts from the rec2-1⁻ mutant, which has a deletion of the N-terminal region of REC2 spanning both the NLS and CBM regions, could be used to obtain active recombinase isolates, there cells that did not, of course, have normal levels of Rec2 activity in vivo. Thus, it appears very likely, if not certain, that the protein fractions, isolated according to the method of Kmiec, E. B., and Holloman, W. K., 1983, CELL 33:857–64, and Eur.J.Bioch. 219:865, were unable to promote homologous recombination in eukaryotic cells.

6.2. Genomic Blots for REC2

In preliminary studies genomic DNA from Ustilago, Saccharomyces, *Aspergillus niger*, mouse and human was digested with EcoR1, BamH1 and Hind III and electrophoresed in 0.8% agarose, transferred to a ZETAPROBE membrane. The membrane was probed with radiolabelled 2.8 kb REC2 insert obtained from the plasmid pCM349 (pET14b-REC2). The membrane was washed in low stringency conditions (40 mM $Na_2PO_4$ 1 mM EDTA, 1% SDS at 50° C.). Strong hybridization was observed in the Ustilago, Saccharomyces, Aspergillus lanes, but not in the mouse or human. Saccharomyces fragments of the following sizes were observed: EcoR1, 5 bands 3.8, 2.9, 2.4, 2.0, and 1.6 Kb; Hind III, 3 bands of 3.8, 2.9, 1.6 Kb; and BamH1 bands of 3.4 Kb and 1.8 Kb.

6.3. The Production of Recombinant REC2 from Ustilago

The 2.5 kb NdeI-XhoI fragment containing Ustilago REC2 was engineered with the NdeI site at the initiation codon using the 2.8 kb BamH1 Ustilago genomic fragment. The NdeI-XhoI fragment was inserted into the corresponding cloning sites in pET-14b (Novagen, Madison Wis.) to yield pCM349. Bacteria carrying pCM349 were deposited in the ATCC as accesion No. 69737 on Jan. 5, 1995. The plasmid pCM349 encodes a Rec2 protein having a leader peptide "MGSSH$_6$SSGLVPRGSH/M etc. (SEQ ID NO:3) which contains a hexahistidine sequence and a thrombin cleavage site (underlined).

*E. coli* transformed with pCM349 were grown in 2×YT (8 g tryptone, 5 g yeast extract, 5 g NaCl per liter) medium containing 35 µg/ml chloramphenicol and 100 µg/ml ampicillin at 37° C. At $A_{590}=0.6$ isopropyl-thio-β-D-galactopyranoside (Sigma Chem. Co.) was added to 1 mM. After 2 hrs the cells were harvested by centrifugation, washed once in BB buffer containing 0.5 mM phenylmethylsulfonylfluoride. Cells were ruptured by sonication (Branson Sonifier 350) with 3 bursts of power for 30 sec each with intermittent cooling in ice water. The broken cell suspension was cleared by centrifugation (15,000 rpm for 20 min, Sorvall SS34) and the supernatant was discarded. The pellet was resuspended in 10 ml BB buffer containing 6M guanidine-HCl and allowed to stand overnight on ice. Insoluble debris was removed by centrifugation and the supernatant (Fraction I) was then loaded onto nitrilotriacetic acid agarose (NTA-agarose, Qiagen, Inc., Chatsworth, Calif.), and immobilized metal affinity column, charged with Ni2+ and equilibrated with BB buffer. The column (1.5 ml) was washed with BB buffer, then eluted stepwise with increasing concentrations of imidazole (60 mM, then 100 mM). REC2 protein eluted with 100 mM imidazole. Fractions (1 ml) were collected and those containing REC2 protein (5 ml) were pooled and dialyzed against TNE buffer (50 mM Tris-HCl, pH 8.5, 100 mM NaCl, 1 mM EDTA) containing 6M urea. After 3 hrs, the dialysis bag was placed in a small beaker and covered with 10 ml of the same buffer. TNE buffer without urea (10 ml) was then added every 15 min until the volume was 200 ml. Failure to remove denaturant by this slow dialysis regimen resulted in precipitation of the REC2 protein. This sample (Fraction II) was then loaded ont a heparin-agarose column (1 ml), followed by a wash (5 ml) with TNE buffer. REC2 protein was eluted with TNE buffer plus 0.25M NaCl and fractions of 0.5 ml were collected. REC2 eluted at tubes 7–9. The pooled peak was dialyzed against TNE buffer containing 10% glycerol, aliquoted, and stored frozen at −70°. The molar extinction coefficient calculated for REC2 protein at 280 nm was $3.16 \times 10^4 M^{-1} cm^{-1}$.

6.4. The Activity of Recombinant REC2

The activity of the recombinant Rec2 protein was determined in three different assays. In each of these assays recombinant Rec2 displayed the same qualitative characteristics that had been observed in the study of the Rec2 fragment obtained from Ustilago.

6.4.1. Materials and Methods

Oligonucleotides: Oligonucleotides were synthesized on an Applied Biosystems 394 nucleic acid synthesizer and purified by capillary electrophoresis. Concentrations were determined spectrophotometrically as total nucleotide using $\epsilon_{260}=8.3 \times 10^3 M^{-1} cm^{-1}$. Oligonucleotides were labeled with $^{32}P$ using polynucleotide kinase and [τ-$^{32}$P]ATP according to van de Sande, J. H., et al., 1973, BIOCHEM. 12:5058. Specific activities of oligonucleotides were $1.5$–$2.5 \times 10^3$ cpm per fmol (as molecules). Hybrid duplexes were prepared by annealing the appropriate complementary oligonucleotides in stoichiometric amounts at 65° C. in 0.4M NaCl for 15 min, then purified and freed of any excess single-stranded oligonucleotide by electrophoresis in D600 gel (AT Biochem, Malvern, Pa.). The duplex oligonucleotide was excised in a band from the gel, then electroeluted and concentrated after precipitation with ethanol.

Hairpins

DNA
5'TAGAGGATCCCCGGGTTTTCCCGGGGATCCTCTAGAGTTTTTCTC3' (SEQ ID NO:4)

DNA/RNA chimera

5'TAGAGGATCCCCGGGTTTTCCCGGGGAUCCUCUAGAGTTTTCTC3' (SEQ ID NO:5)

Duplexes 72-mer
5'-TTACGAATTCGAGCTCGGTACCCGGGGATCCTCTAGAGTCGACCTGCAGGCATGCAAGCTTGGCACTGGCCG3'∞0 (SEQ ID NO:6)
3'-AATGCTTAAGCTCGAGCCATGGGCCCCTAGGAGATCTCAGCTGGACGTCCGTACGTTCGAACCGTGACCGGC5'∞0 (SEQ ID NO:7)

50-mer
5'TTACGAATTCGAGCTCGGTACCCGGGGATCCTCTAGAGTCGACCTGCAGG3' (SEQ ID NO:8)
3'AATGCTTAAGCTCGAGCCATGGGCCCCTAGGAGATCTCAGCTGGACGTCC5' (SEQ ID NO:9)

30-mer
5'TTACGAATTCGAGCTCGGTACCCGGGGATC3' (SEQ ID NO:10)
3'AATGCTTAAGCTCGAGCCATGGGCCCCTAG5' (SEQ ID NO:11)

or RNA 30-mer
3'AAUGCUUAAGCUCGAGCCAUGGGCCCCUAG5' (SEQ ID NO:12)

Reactions: Joint molecule formation was measured by a filter retention assay in which complexes comprised of single-stranded and duplex DNA molecules were trapped on nitrocellulose filters. The assay was developed by Bianchi, M., et al., 1983, CELL 34:931, to measure metastable intermediates that may not survive removal of protein. Samples (20 μl) were withdrawn into 1 ml of 10×SSC (SSC is 0.15M NaCl, 0.015M Na citrate, pH 7.8) without deproteinization and the mixture passed on to a nitrocellulose filter (BA85, 0.45 μ filter, Schleicher & Schuell, Keene, NH) that had been soaked extensively in water followed by a rinse in 10× SSC. Filters were washed twice with 1 ml of 10× SSC, then dried under a heat lamp, and the bound radioactive DNA quantitated by scintillation counting in Econofluor (Dupont NEN).

Identical strand pairing reactions were carried out essentially the same as the described by Rao, B. J., and Radding, C. M., 1993, PROC.NATL.ACAD.SCI. 90: 6646, except that the carrier DNA used was polyd|A-T| rather than heterologous single stranded oligonucleotide. Reactions contained M13 single stranded circular DNA, and $^{32}$P-labeled oligonucleotide. The identical strand oligonucleotide was a 33-mer 5'ACAGCACCAGATTCAGCAATTAAGCTCTAAGCC3' (SEQ ID NO:13) which corresponds to residues 207–239 of M13 DNA (van Wezenbeek, P. M. G. F., et al., 1980, GENE 11:129). Control reactions measuring hybrid DNA formation between complementary antiparallel sequences utilized M13mp18 DNA and $^{32}$P-labeled 44-mer 5'GAATTC-GAGCTCGGTACCCGGGGATCCTCTA-GAGTCGACCTGCA3' (SEQ ID NO:14) which corresponds to residues 412–455 of M13mp18 DNA.

Renaturation reactions were carried out by monitoring the increase in resistance of denatured P22 |$^{3}$H|DNA to digestion by S1 nuclease as described before (Kmiec, E. J., and Holloman, W. H., 1994, EUR.J.BIOCHEM. 219:865). ATPase activity was measured in reactions (per 50 μl) containing 25 mM Tris-HCl, pH7.5, 10 mM MgCl$_2$, 1 mM DTT, 20 μM M13 DNA, 0.5 mM |τ$_{-32}$P|ATP at $10^5$ cpm per nmol. Reactions were started by addition of REC2 protein, conducted at 37°, and quenched by addition of 100 μl 10 mM potassium phosphate, 100 μl acetone, 50 μl ammonium molybdate in 4N H$_2$SO$_4$, 700 μl isobutanol:benzene (1:1). After the mixture was vortexed and the phases separated, half (350 μl) of the organic phase (top) was removed and the radioactivity determined by Cerenkov counting.

Renaturation reactions (40 μl) were performed using 20 μM denatured P22 |$^{3}$H|DNA (as nucleotide) either in the presence of 1 mM ATP or with no ATP. Reaction were carried out at 37° for 30 min. DNA renatured indicates the level of input DNA that became resistant to digestion by S1 nuclease. In general only 80–85%, of the DNA could be converted to a form resistant to Si hydrolysis. The data presented are uncorrected for this value. Protein independent renaturation was <5%.

ATPase reactions were performed as described above in the presence or absence of 20 μM M13 DNA (as nucleotide) at 37° for 15 min.

Identical strand pairing reactions were carried out in a total volume of 200 μl which contained 25 mM Tris acetate, pH 7.5, 10 MM Mg$^2$+ acetate, 1 mM dithiothreitol, 1 mM ATP, 100 μg/ml bovine serum albumin, 10 μM polyd|A-T| (as nucleotide), 0.41 nM M13 single stranded circular DNA (as molecules), and 0.85 nM 32P-labeled identical strand 33-mer oligonucleotide (as molecules). Reactions were initiated by addition of REC2 protein to 0.5 μM, incubated at 37°, and samples (20 μl) removed. Reactions were then stopped by addition of 200 μl reaction buffer minus DNA and the mixture immediately centrifuged through Ultrafree-MC cellulose filters (Millipore) at 2000×g for 6 min in a table top centrifuge. Filters were washed with an additional 100 μm of buffer, centrifuged for 3 min and the radioactivity bound then determined. In the absence of M13 single-stranded DNA the background of $^{32}$P label retained was usually 5% of the input labeled oligonucleotide. Results are corrected for this background.

Complementary strand pairing reactions were carried out using M13mp18 DNA and complementary antiparallel sequence oligonucleotide 44-mer (200 μl) utilized 0.47 nM M13mp18 DNA and 1.14 nM $^{32}$P-labeled 44-mer and were processed as above.

Formation of DNA/DNA and DNA/RNA hybrids were formed as follows. DNA/DNA duplex fragments were prepared by annealing two complementary $^{32}$P-labeled oligonucleotides of the indicated lengths and purified as described by gel electrophoresis. The sequences utilized spanned the multiple cloning site of M13mp19 DNA. Pairing reactions contained 25 mM Tris-HCl, pH 7.5, 10 mM MgCl$_2$, 1 mM ATP, 1mM dithiothreitol, 0.3 nM M13mp19 single-stranded circular DNA (as molecules), 0.23 nM duplex $^{32}$P DNA fragment (as molecules) and 0.25 μM REC2 protein. At the appropriate time aliquots were removed and joint molecules then determined. RNA/DNA duplexes fragments were prepared by hybridizing either complementary sequence DNA oligonucleotides or else complementary RNA and DNA oligonucleotides were tested for pairing. In this latter case the RNA strand was complementary to the M13mp19 multiple cloning region. In both cases only the (+) DNA strand oligonucleotides were radiolabelled.

Joint molecule formation with chimeric hairpin duplex oligonucleotides were performed as follows. Self-complementary DNA or mixed DNA-RNA chimeric oligonucleotide 44-mer sequences were synthesized on an Applied Biosystems 394 DNA/RNA synthesizer. After labeling at the open 5'-OH with |γ–$^{32}$p|ATP and polynucleotide kinase the hairpin was sealed with DNA ligase. Homologous pairing with an RNA/DNA oligonucleotide hairpin. Joint molecule formation was performed as described above in reactions containing 25 mM Tris-HCl, pH 7.5, 10 mM MgCl$_2$, 1 mM ATP, 1 mM dithiothreitol, 0.45 nM M13mp18 or M13mp19 DNA (as molecules), 1.1 nM $^{32}$P-labeled oligonucleotide, and 0.5 μm REC2 protein. Aliquots (20 μl) were removed to 1 ml of 10× SSC and joint molecule formation was measured after washing onto nitrocellulose filters.

6.4.2. Results

6.4.2.1. Expression of the Recombinant REC2 Protein

As described in section 6.3, a 2.5 kbp genomic DNA fragment with the REC2 open reading frame engineered to contain an NdeI site at the initiation methionine codon was inserted behind the ø10 bacteriophage T7 promoter in the pET vector system which is designed for over-expression of genes in *E. coli.* (Studier, F. W., and Moffatt, B. A., 1986, J.MOL.BIOL. 189:113). After induction with IPTG, a protein with a mass of ~110 kDa accumulated in the cells as determined by SDS-gel electrophoresis. In a control in which cells contained the vector without the REC2 gene, no accumulation of the 110 kDa protein was noted. With the use of antiserum obtained from rabbit immunized with a 12 kDa fusion protein containing 96 amino acid residues from the carboxy terminus of the REC2 protein, it was determined that the 110 kDa protein cross-reacted. While the bulk of the overexpressed protein was insoluble, a small fraction (~5%) remained soluble even in low ionic strength buffer. This soluble 110 kDa protein was purified with the aid of the antiserum as a REC2-specific reagent following chromatography on heparin agarose and fast protein liquid chromatography (FPLC) separation on a Pharmacia MonoS column. N-terminal amino acid sequence determination of 15 residues confirmed the identity of the 110 kDa protein as REC2. Since the predicted mass of REC2 is only 84 kDa, it is concluded that the protein runs anomalously under conditions of SDS-gel electrophoresis.

To enable purification of the protein a 2.5 kbp DNA fragment containing the REC2 gene was inserted into pET14b, which was designed for expression of fusion proteins preceded by a hexa-histidine leader sequence. Due to the utility of the histidine-leader sequence in affinity chromatography, the hexa-histidine-REC2 fusion was considered more amenable for biochemical studies. After induction of cells with IPTG the insoluble fraction containing the bulk of the REC2 protein was collected and dissolved in guanidine-HCI (Fraction 1). REC2 protein was then isolated using immobilized metal affinity chromatography. The denatured protein bound stably to a $Ni^{2+}$-NTA column and contaminating proteins which lacked the histidine leader were removed by extensive washing. Inclusion of 0.5M salt in the buffer reduced nonspecific ionic interaction of contaminating proteins. REC2 protein was eluted with an increasing gradient of imidazole, then renatured after exchanging the guanidine-HCI for urea, followed by gradual stepwise removal of urea. The resulting fraction containing highly purified REC2 protein was completely soluble (Fraction II) and was further purified by chromatography on heparin-agarose (Fraction M). Protein in the final fraction was comprised largely of the 110 kDa REC2 protein although a few other lower molecular weight proteins were evident upon close inspection. It was considered that these were likely to be proteolytic degradation products since (i.) no such protein bands were evident in similarly processed preparations of extracts made from cells not overexpressing REC2 and (ii.) the level of these protein bands increased with a concomitant decrease in the 110 kDa band as a result of prolonged handling of cell extracts in the initial processing (not shown).

6.4.2.2. Reannealing of Complementary Strands of DNA

The purified Rec2 protein promoted the reannealing of complementary single strands of P22 viral DNA, in an ATP dependent manner, and catalyzed a DNA-dependent ATP hydrolysis. See FIG. 3A and 3B. The turnover number for the ATP hydrolytic reaction was calculated as 5.3 /minute, which is below the 225 /minute rate calculated in kinetic studies on the 70 kDa fragment of Rec2 obtained from Ustilago extracts.

6.4.2.3. Reannealing of a 33-MER to Single Stranded, Circular DNA

Homologous pairing activity of the REC2 protein was demonstrated using an assay that is free from interference by reaction leading to heteroduplex formation that can occur through simple second-order renaturation of complementary single strands of DNA (for review see Kmiec, E. B., and Holloman, W. K., 1994, J.BIOL.CHEM. 269:10163). This assay measures identical sequence recognition and was first reported for RecA protein by Rao, B. J., and Radding, C. M., 1993, PROC.NATL.ACAD.SCI. 90:6646. An oligonucleotide (33-mer) of identical sequence and polarity as residues 207-251 of bacteriophage Mi 3 was synthesized and labeled with $^{32}P$ at the 5'-end. When this identical sequence oligonucleotide was present in a reaction at a two-fold molar excess over M 13 single stranded circles, REC2 protein promoted formation of a specific complex between the oligonucleotide and M13 DNA that could be trapped on a membrane filter. The complex that formed was completely dependent on ATP (FIG. 4A) and was composed of almost exactly one mole of oligonucleotide per mole of M13 DNA as molecules. No stable complex formed when M13 DNA was replaced by øX174 single-stranded circles or when ADP was included in the reaction. The complex was completely dissociated by addition of proteinase K.

In a control reaction using an oligonucleotide complementary and anti parallel to M13 sequence, stable complexes were also formed (FIG. 4B). Interestingly, the stoichiometry of DNAs in the complex was approximately 2 moles of oligonucleotide per mole of M13 single stranded circles. After treatment with Proteinase K the ratio dropped to approximately 2 to 2 as would be expected for formation of a heteroduplex joint stabilized through Watson-Crick base pairing.

6.4.2.4. Size Dependence of Duplex Formation

A series of duplex DNA oligonucleotides of defined lengths was tested for activity in joint molecule formation in a study aimed at exploring the minimum length requirement for homologous pairing by REC2 protein. Joint molecule formation was monitored in reactions containing radiolabelled duplex DNA and homologous single-stranded circular M13 DNA. Joint molecules were assayed by measuring retention of labeled DNA on nitrocellulose filters. In reactions containing a duplex 70-mer, there was efficient joint molecule formation, but when a 50-mer was used the level dropped markedly (FIG. 5A). No joint molecules could be detected when the duplex was 30 bp in length. Thus, in the case of REC2 there is a minimum length requirement for joint molecule formation that is between 5 and 7 turns of duplex, well above that necessary for stabilizing DNA in the double-stranded conformation Thomas, C. A., 1966, PROG..NUC.ACID RES.MOL.BIOL. 5:315.

When the 30-mer was composed of an RNA/DNA hybrid there was considerable joint molecule formation (FIG. 5B). The polarity of the RNA directed the reaction. Complexes were formed when the RNA sequence was complementary to the M13 DNA sequence, but not when it was identical. Activity of hairpin duplexes in joint molecule formation When the substrates in pairing reactions include linear duplex molecules and single stranded circular DNA, interpretation of pairing data can be complicated by the contribution of complementary strand hybridization to said exchange (Kmiec, E. B. and Holloman, W. K., 1994, J.BI-OL.CHEM. 269:10163). To study the influence of RNA on the homologous pairing aspect of the reaction in isolation without complication from the strand exchange aspect, a duplex substrate was devised that could serve as a reactant for homologous pairing but which would be topologically barred from proceeding past that phase on the reaction pathway. This was a linear heteroduplex of RNA and DNA with hairpin caps on both ends (FIG. 6A). It was prepared by synthesis of a single 44-mer oligonucleotide which contained an inverted repeat of complementary sequences. The sequence was designed so that intramolecular association of complementary sequences would result in formation of a linear duplex with hairpin ends. There was a total of 18 base pairs in the duplex region. Along one strand was a stretch of 18 residues composed entirely of DNA nucleotides. Along the other strand were the 18 complementary residues, 15 of which in contiguous array were RNA nucleotides. At the ends were caps of 4 residues each of oligo dT connecting the complementary strands. The hairpin molecule was labeled at the single open 5'-end with [γ-32P]ATP and polynucleotide kinase, then sealed with DNA ligase, yielding a covalently closed linear duplex. Homologous pairing with single stranded circular DNA as catalyzed by REC2 protein was highly efficient reaching almost 1 molecule of hairpin duplex (see FIG. 6B) per molecule of single-stranded circular DNA.

When the length of the RNA stretch was reduced by systematic replacement of the ribonucleotide residues with deoxyribonucleotide counterparts, the pairing efficiency decreased but did not drop to zero even when only 3 RNA residues remained (FIG. 7). When all of the nucleotides residues present were deoxyribonucleotides there was no reaction. Thus, addition of RNA to a duplex can activate it for pairing under conditions where a completely DNA duplex is inactive. Furthermore, addition of RNA to a duplex brings the minimum homology threshold required for REC2-catalyzed pairing in line with the minimum threshold of length necessary for duplex stability.

6.5. The Use of Recombinant REC2 to Promote Homologous Recombination

The purified Recombinant Rec2 was used to promote homologous recombination in the iso-1-cytochrome c mutant Saccharomyces system developed by Moerschell, R. P. et al., 1988, PROC.NATL.ACAD.SCI. 85:524. Briefly, a frame shift mutation caused by the deletion of one nucleotide prevents the growth of mutant strain on low grade carbon sources. A ssDNA 50-mer containing the wild type sequence extending from 14 bp 5' of the deletion to 36 bp 3' of it is complexed with recombinant Rec2, dialyzed into 2 mM Tris HCl (pH=7.5) by incubation at 31° C. for 10 minutes at a concentration of 20 ng ssDNA/μl. The Rec2 protein was present in 5 and 10 fold molar excess. Thereafter the complex is mixed with $10^6$ mutant Saccharomyces in a final volume of 25 μl, incubated on ice for 20 minutes and electroporated into the cells. The results presented in FIG. 8 indicate that the presence of Rec2 at a protein:oligonucleotide molar ratio of 5:1 cause an approximately 10 fold increase in the rate of wild type transformants. In the linear portion of the dose-response curve the rate without Rec2 was 0.6 transformants per $10^6$ cells per ng DNA; with a 10× molar ratio of Rec2 present the rate increased to 8.4 transformants per $10^6$ cells per ng DNA.

6.6. The Use of REC2 (T→A)$^{697}$ Expression Vector to Promote Homologous Recombination in Ustilago

6.6.1. Construction of the (T→A)$^{697}$ Expression Vector

Site directed mutations were introduced into the REC2 gene by the method of Ho, S. N., et al., 1989, GENE 77:51–59. Briefly, a first PCR reaction generates two REC2 gene fragments having overlapping ends that contain the desired mutation. The fragments are denatured and reannealed together. Heteroduplexes are formed by pairing at the 3' ends, which can then be extended to yield a fully duplex fragment that spans the combined sequence of the two PCR fragments. In a second round of PCR, this spanning fragment is amplified, cloned and thereafter inserted into the REC2 gene. Using this technique the Thr codon (ACG) at position 697 was mutated to an Ala codon (GCG), this gene is termed REC2-10 hereinafter.

6.6.2. Results Showing the Rate of Homologous Recombination

To test the activity of REC2-10 the plasmid pCM441/REC2 and pCM441/REC2-10 were constructed that lack a Ustilago replication origin and contains a 3.2 kb fragment spanning the REC2 and REC2-10 genes, respectively and a modified ADE1 gene of U. *maydis*, on a 5.0 kbp BamHI-XbaI fragment that was isolated by complementing the adenine auxotrophy of the ade1-1 mutant. The ADE-1 gene was modified by removing an essential 100 bp NcoI fragment from within the coding region of the gene. The NcoI created gap within the ADE1 gene does not overlap the ade1-1 lesion, yet enables transformation of ade1-1 strains to adenine prototrophy upon a recombination of the ade1-1 gene and the circular pCM441 plasmid at a site between the ade1-1 lesion and the NcoI deletion. The experimental system is described in greater detail in Rubin, B. P. et al., 1994, MOL.CELL.BIOL. 14:6287–96, which is hereby incorporated by reference in its entirety.

The results of transformation with either pCM441/REC2 and pCM441/REC2-10 of wild-type Ustilago and of the rec2-1 strain lacking a functional Rec2 are shown below.

TABLE I

| Plasmid | Transformants per 5 μg | |
| --- | --- | --- |
| | rec2-1 | w.t. |
| pCM441 | 1 | 76 |
| pCM441/REC2 | 83 | 90 |
| pCM441/REC2-10 | 720 | 665 |

These data show that the REC2-10 gene can cause a rate of homologous recombination in a wild type eukaryotic cell 8–10 fold greater than that of the wild type cell. Bacteria carrying the plasmid pCM441/REC2-10 were deposited in the ATCC on Jan. 10, 1995 as accession No. 69740 with the designation BCM677.

6.7. The Construction of a REC2 Vector for Expression in Mammalian Cells

The REC2 mammalian expression vector utilizing the CMV promoter and the poly A region of bovine growth hormone was constructed as follows. A 130 bp fragment of the 5' region of Ustilago REC2 was PCR amplified by two primers. The 5' primer contained a Bam HI cloning site and CACC sequence prior to the AUG codon for efficient translation. The 3' primer contained a region spanning a unique MunI restriction site in Ustilago REC2 sequence. The PCR amplified fragment was digested by BamHI and MunI restriction enzymes and gel purified. A mammalian expression vector pCDNA3 was digested by BamHl and XhoI restriction enzymes. Also, the 2.9 kb fragment containing Ustilago REC2 was isolated by MunI and BamHI digestion of pET14 REC2 vector. These three purified fragments, 130 bp of PCR amplified region of the REC2, 2.9 kb of REC2 sequence, and 5.4 kb of pCDNA3 were ligated together at equal molar ratios and the ligation mixture was transformed into DH5α competent cells. Several clones were sequenced and shown to have a correct sequence within the 130 bp PCR amplified region. This vector also contained a neomycin resistance gene expressed from SV40 early promoter enabling selection of permanent clones by G418 resistance. Bacteria carrying the resultant plasmid pCMV-REC2 were deposited in the ATCC on Jan. 5, 1995 as accession No. 69738

We claim:

1. A polydeoxynucleic acid expression vector for expressing a recombinase in a higher eukaryotic cell comprising:
    a. a coding portion encoding a protein that:
        (1) is an ATPase;
        (2) catalyzes the formation of complementary or identical strand pairings of polydeoxynucleic acids; and (3) promotes homologous recombination in a eukaryote;

(4) wherein the normalized alignment score of the protein, compared to SEQ ID NO: 2, is at least about 150;

(5) wherein said coding portion hybridizes to the 2.8 Kb Bam HI REC2 insert of pCM346 when the coding portion is membrane immobilized and the final wash conditions are 40 mM $Na_2PO_4$, 1 mM EDTA, 1% SDS at 50° C.;

(6) wherein said coding portion is a naturally occurring REC2 gene or a naturally occurring REC2 gene modified to remove a $p34^{CDC2}$ kinase consensus phosphorylation site; and b. a promoter operably linked to the coding portion, said promoter being active in a higher eukaryotic cell.

2. The vector of claim 1 wherein the promoter is a mammalian or viral promoter.

3. The vector of claim 1 which is pCMV-REC2, deposited as ATCC No. 69738.

4. The vector of claim 1 which further comprises a selectable marker gene.

5. The vector of claim 1, wherein the coding portion encodes a protein comprising a recombinase of an ascomycetes yeast form fungal cell.

6. The vector of claim 1, wherein the coding portion encodes a protein comprising a recombinase of an ascomycetes yeast form fungal cell that has been modified by the deletion of a $p34^{CDC2}$ kinase consensus phosphorylation site.

7. The vector of claim 1, wherein the coding portion encodes a protein comprising a recombinase of a fungus selected from the group of fungal genera consisting of Ustilago, Saccharomyces and Aspergillus.

8. The vector of claim 1, wherein the coding portion encodes a protein comprising a recombinase of a fungus selected from the group of fungal genera consisting of Ustilago, Saccharomyces and Aspergillus, which protein has been modified by the deletion of a $p34^{CDC2}$ kinase consensus phosphorylation site.

9. The vector of claim 1, wherein the normalized alignment score is at least about 200.

10. The vector of claim 9, wherein the coding portion encodes a protein comprising a recombinase of an ascomycetes yeast form fungal cell.

11. The vector of claim 9, wherein the coding portion encodes a protein comprising a recombinase of an ascomycetes yeast form fungal cell that has been modified by the deletion of a $p34^{CDC2}$ kinase consensus phosphorylation site.

12. The vector of claim 9, wherein the coding portion encodes a protein comprising a recombinase of a fungus selected from the group of fungal genera consisting of Ustilago, Saccharomyces and Aspergillus.

13. The vector of claim 9, wherein the coding portion encodes a protein comprising a recombinase of a fungus selected from the group of fungal genera consisting of Ustilago, Saccharomyces and Aspergillus, which protein has been modified by the deletion of a $p34^{CDC2}$ kinase consensus phosphorylation site.

14. A polydeoxynucleic acid expression vector for expressing a recombinase in a higher eukaryotic cell comprising:

a. a coding portion encoding a protein that:
(1) is an ATPase;
(2) catalyzes the formation of complementary or identical strand pairings of polydeoxynucleic acids; and
(3) promotes homologous recombination in a eukaryote;

(4) wherein the normalized alignment score of the protein, compared to SEQ ID NO: 2, is at least about 150;

(5) wherein said coding portion hybridizes to the 2.8 Kb Bam HI REC2 insert of pCM346 when the coding portion is membrane immobilized and the final wash conditions are 40 mM $Na_2PO_4$, 1 mM EDTA, 1% SDS at 50° C.;

(6) wherein said coding portion is a naturally occurring REC2 gene that lacks or has been modified to lack a $p34^{CDC2}$ kinase consensus phosphorylation site; and b. a promoter operably linked to the coding portion, said promoter being active in a higher eukaryotic cell.

15. The vector of claim 14 wherein the normalized alignment score is at least about 200.

16. A polydeoxynucleic expression vector for expressing a recombinase in a prokaryotic cell comprising:

a. a coding portion encoding a protein that:
(1) is an ATPase;
(2) catalyzes the formation of complementary or identical strand pairings of polydeoxynucleic acids; and
(3) promotes homologous recombination in a eukaryote;

(4) wherein the normalized alignment score of the protein, compared to SEQ ID NO: 2, is at least about 150;

(5) wherein said coding portion hybridizes to the 2.8 Kb Bam HI REC2 insert of pCM346 when the coding portion is membrane immobilized and the final wash conditions are 40 mM $Na_2PO_4$, 1 mM EDTA, 1% SDS at 50° C.;

(6) wherein said coding portion is the coding portion of a naturally occurring REC2 gene or of a naturally occurring REC2 gene modified to remove a $p34^{CDC2}$ kinase consensus phosphorylation site; and b. a promoter operably linked to the coding portion, said promoter being active in the prokaryotic cell.

17. The vector of claim 16 which is pCM349 deposited as ATCC NO. 69737.

18. The vector of claim 16, wherein the coding portion encodes a protein comprising a recombinase of an ascomycetes yeast form fungal cell.

19. The vector of claim 16, wherein the coding portion encodes a protein comprising a recombinase of an ascomycetes yeast form fungal cell that has been modified by the deletion of a $p34^{CDC2}$ kinase consensus phosphorylation site.

20. The vector of claim 16, wherein the coding portion encodes a protein comprising a recombinase of a fungus selected from the group of fungal genera consisting of Ustilago, Saccharomyces and Aspergillus.

21. The vector of claim 16, wherein the coding portion encodes a protein comprising a recombinase of a fungus selected from the group of fungal genera consisting of Ustilago, Saccharomyces and Aspergillus that protein has been modified by the deletion of a $p34^{CDC2}$ kinase consensus phosphorylation site.

22. The vector of claim 16, wherein the normalized alignment score is at least about 200.

23. The vector of claim 22, wherein the coding portion encodes a protein comprising a recombinase of an ascomycetes yeast form fungal cell.

24. The vector of claim 22, wherein the coding portion encodes a protein comprising a recombinase of an ascomycetes yeast form fungal cell that has been modified by the deletion of a $p34^{CDC2}$ kinase consensus phosphorylation site.

25. The vector of claim 22, wherein the coding portion encodes a protein comprising a recombinase of a fungus selected from the group of fungal genera consisting of Ustilago, Saccharomyces and Aspergillus.

26. The vector of claim 22, wherein the coding portion encodes a protein comprising a recombinase of a fungus selected from the group of fungal genera consisting of Ustilago, Saccharomyces and Aspergillus, which protein has been modified by the deletion of a $p34^{CDC2}$ kinase consensus phosphorylation site.

* * * * *

UNITED STATES PATENT AND TRADEMARK OFFICE
CERTIFICATE OF CORRECTION

PATENT NO. : 5,780,296
DATED : July 14, 1998
INVENTOR(S) : William K. Holloman and Eric B. Kmiec It is certified that error appears in the above-identified patent and that said Letters Patent is hereby corrected as shown below:

Title page item [73],

Assignee: Thomas Jefferson University, Philadelphia, PA. and Cornell Research Foundation, Inc., Ithaca, N.Y.

Signed and Sealed this

Second Day of February, 1999

Attest:

Attesting Officer

*Acting Commissioner of Patents and Trademarks*

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 3206 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 177..2520

( x i ) SEQUENCE DESCRIPTION: SEQ ID NO:1:

```
AATATTCACG  ATTCTGATGT  GGAAGCGTAA  GGAGAAGCAG  ATTAGGTGCT  GGTAGGAGCA         60

CCTCAACAAG  CTAGCCGCCT  TGTCGTGCTC  ATCCCAGTCT  TCCACAGCCC  CAACCATCGT        120

AGCGGCTGCG  CATCGCCACG  AATGGTTGCG  ACTCACAGCT  TTGCACGTGC  TAAATC            176

ATG  ACT  GGC  ATC  GCG  ATC  GCC  GAT  GTT  GGC  TGC  ATT  TCG  AAA  CGC  ATC    224
Met  Thr  Gly  Ile  Ala  Ile  Ala  Asp  Val  Gly  Cys  Ile  Ser  Lys  Arg  Ile
 1              5                  10                  15

AAG  GCG  TGC  TGT  CGT  CGA  GCA  AAG  CTC  TTC  AGT  ACC  GAC  GAG  ATC  CTC    272
Lys  Ala  Cys  Cys  Arg  Arg  Ala  Lys  Leu  Phe  Ser  Thr  Asp  Glu  Ile  Leu
              20                  25                  30

CTC  AGC  CCA  CCG  CAG  CAA  TTG  GCA  CAC  GTG  TTG  CGC  ATA  TCC  CAA  GCA    320
Leu  Ser  Pro  Pro  Gln  Gln  Leu  Ala  His  Val  Leu  Arg  Ile  Ser  Gln  Ala
         35                  40                  45

GAT  GCC  GAT  CTG  CTT  CTT  CTC  CAA  GTG  GCC  ACG  GCA  TCT  GCT  CCA  CCT    368
Asp  Ala  Asp  Leu  Leu  Leu  Leu  Gln  Val  Ala  Thr  Ala  Ser  Ala  Pro  Pro
     50                  55                  60

CCC  ATC  TCG  GTA  CTC  GAT  GCG  CTC  AAT  GGC  AAG  CTT  CCT  GCT  ACC  AAC    416
Pro  Ile  Ser  Val  Leu  Asp  Ala  Leu  Asn  Gly  Lys  Leu  Pro  Ala  Thr  Asn
 65                  70                  75                  80

CTG  GAC  CAG  AAC  TTC  TTT  GAC  GCC  GTC  GCA  GCT  GCT  GAC  GAT  GAC  GAC    464
Leu  Asp  Gln  Asn  Phe  Phe  Asp  Ala  Val  Ala  Ala  Ala  Asp  Asp  Asp  Asp
                 85                  90                  95

GAC  GAC  AAT  GAT  GAT  GAC  GAT  GAC  AAA  GCC  GAT  TCC  GGT  TCG  GCC  GAC    512
Asp  Asp  Asn  Asp  Asp  Asp  Asp  Asp  Lys  Ala  Asp  Ser  Gly  Ser  Ala  Asp
             100                 105                 110

GCT  TCA  GAC  ACG  AGC  GAT  GCG  GAT  GAT  CAA  CAT  CTC  AAC  GAC  GCA  AGG    560
Ala  Ser  Asp  Thr  Ser  Asp  Ala  Asp  Asp  Gln  His  Leu  Asn  Asp  Ala  Arg
         115                 120                 125

TTT  GCA  TCG  TCT  TGC  ATC  GTG  CCC  CCA  ACA  CAG  GGG  TAC  GAT  GGC  AAC    608
Phe  Ala  Ser  Ser  Cys  Ile  Val  Pro  Pro  Thr  Gln  Gly  Tyr  Asp  Gly  Asn
     130                 135                 140

TTT  CCC  GGC  GCA  CAA  TGC  TTT  GTC  TAC  GAT  TCC  GAT  GCC  GGC  TCG  GAC    656
Phe  Pro  Gly  Ala  Gln  Cys  Phe  Val  Tyr  Asp  Ser  Asp  Ala  Gly  Ser  Asp
 145                 150                 155                 160

AGT  GAT  GCA  CGC  AGT  AGC  ATC  GAC  GCT  GTG  ATG  CAC  GAA  GAT  ATC  GAG    704
Ser  Asp  Ala  Arg  Ser  Ser  Ile  Asp  Ala  Val  Met  His  Glu  Asp  Ile  Glu
```

-continued

|  |  |  | 165 |  |  |  | 170 |  |  |  | 175 |  |  |  |  |
|---|---|---|---|---|---|---|---|---|---|---|---|---|---|---|---|
| CTA | CCG | TCC | ACC | TTT | TGC | CGT | CCA | CAA | ACA | CCA | CAA | ACC | CAC | GAT | GTT | 752 |
| Leu | Pro | Ser | Thr | Phe | Cys | Arg | Pro | Gln | Thr | Pro | Gln | Thr | His | Asp | Val |  |
|  |  |  | 180 |  |  |  | 185 |  |  |  | 190 |  |  |  |  |
| GCC | CGT | GAC | GAG | CAT | CAT | GAT | GGG | TAT | CTT | TGC | GAT | CCC | AAA | GTT | GAC | 800 |
| Ala | Arg | Asp | Glu | His | His | Asp | Gly | Tyr | Leu | Cys | Asp | Pro | Lys | Val | Asp |  |
|  |  | 195 |  |  |  | 200 |  |  |  | 205 |  |  |  |  |  |
| CAC | GCC | TCG | GTC | GCC | AGA | GAC | GTC | TTA | TCG | CTC | GGA | CGC | CAA | CGA | CAT | 848 |
| His | Ala | Ser | Val | Ala | Arg | Asp | Val | Leu | Ser | Leu | Gly | Arg | Gln | Arg | His |  |
|  | 210 |  |  |  | 215 |  |  |  | 220 |  |  |  |  |  |  |
| GTA | TTC | TCA | AGC | GGC | TCC | CGA | GAG | CTC | GAC | GAC | CTG | CTA | GGC | GGT | GGG | 896 |
| Val | Phe | Ser | Ser | Gly | Ser | Arg | Glu | Leu | Asp | Asp | Leu | Leu | Gly | Gly | Gly |  |
| 225 |  |  |  |  | 230 |  |  |  | 235 |  |  |  |  |  | 240 |
| GTG | CGT | TCC | GCT | GTG | CTC | ACC | GAG | CTC | GTC | GGT | GAA | AGC | GGC | TCT | GGT | 944 |
| Val | Arg | Ser | Ala | Val | Leu | Thr | Glu | Leu | Val | Gly | Glu | Ser | Gly | Ser | Gly |  |
|  |  |  |  | 245 |  |  |  | 250 |  |  |  | 255 |  |  |  |
| AAG | ACC | CAG | ATG | GCT | ATC | CAA | GTT | TGC | ACT | TAT | GCC | GCT | CTC | GGC | TTG | 992 |
| Lys | Thr | Gln | Met | Ala | Ile | Gln | Val | Cys | Thr | Tyr | Ala | Ala | Leu | Gly | Leu |  |
|  |  |  | 260 |  |  |  | 265 |  |  |  | 270 |  |  |  |  |
| GTT | CCG | CTG | AGC | CAA | GCT | GAC | GAT | CAC | GAC | AAG | GGC | AAC | AAC | ACA | TTT | 1040 |
| Val | Pro | Leu | Ser | Gln | Ala | Asp | Asp | His | Asp | Lys | Gly | Asn | Asn | Thr | Phe |  |
|  |  | 275 |  |  |  | 280 |  |  |  | 285 |  |  |  |  |  |
| CAA | TCC | AGG | ACT | TTC | GTA | CGA | GAC | CCG | ATA | CAC | GCT | TCG | ACC | AAA | GAC | 1088 |
| Gln | Ser | Arg | Thr | Phe | Val | Arg | Asp | Pro | Ile | His | Ala | Ser | Thr | Lys | Asp |  |
|  | 290 |  |  |  | 295 |  |  |  | 300 |  |  |  |  |  |  |
| GAC | ACA | CTA | AGC | GAC | ATT | CTG | CAG | AGC | TAC | GGC | ATG | GAG | CCC | TCG | ATT | 1136 |
| Asp | Thr | Leu | Ser | Asp | Ile | Leu | Gln | Ser | Tyr | Gly | Met | Glu | Pro | Ser | Ile |  |
| 305 |  |  |  | 310 |  |  |  | 315 |  |  |  |  |  |  | 320 |
| GGA | TCT | CAC | CGC | GGT | ATG | GGC | GCG | TGC | TAC | ATC | ACA | TCT | GGT | GGC | GAG | 1184 |
| Gly | Ser | His | Arg | Gly | Met | Gly | Ala | Cys | Tyr | Ile | Thr | Ser | Gly | Gly | Glu |  |
|  |  |  | 325 |  |  |  | 330 |  |  |  |  |  |  | 335 |  |
| CGC | GCA | GCG | CAT | TCG | ATC | GTG | AAC | CGA | GCT | CTG | GAA | CTT | GCA | AGC | TTT | 1232 |
| Arg | Ala | Ala | His | Ser | Ile | Val | Asn | Arg | Ala | Leu | Glu | Leu | Ala | Ser | Phe |  |
|  |  |  | 340 |  |  |  | 345 |  |  |  | 350 |  |  |  |  |
| GCT | ATC | AAC | GAA | CGC | TTT | GAT | CGC | GTC | TAT | CCG | GTC | TGC | GAT | CCT | ACA | 1280 |
| Ala | Ile | Asn | Glu | Arg | Phe | Asp | Arg | Val | Tyr | Pro | Val | Cys | Asp | Pro | Thr |  |
|  |  | 355 |  |  |  | 360 |  |  |  | 365 |  |  |  |  |  |
| CAA | AGC | TCG | CAG | GAC | GCC | GAT | GGG | CGC | CGC | GAC | GCA | TTG | CTG | GCC | AAG | 1328 |
| Gln | Ser | Ser | Gln | Asp | Ala | Asp | Gly | Arg | Arg | Asp | Ala | Leu | Leu | Ala | Lys |  |
|  | 370 |  |  |  | 375 |  |  |  | 380 |  |  |  |  |  |  |
| GCA | CAG | CAG | CTT | GGT | CGT | CGA | CAA | GCG | CTT | GCC | AAC | TTG | CAC | ATA | GCC | 1376 |
| Ala | Gln | Gln | Leu | Gly | Arg | Arg | Gln | Ala | Leu | Ala | Asn | Leu | His | Ile | Ala |  |
| 385 |  |  |  |  | 390 |  |  |  | 395 |  |  |  |  |  | 400 |
| TGC | GTC | GCT | GAT | GTC | GAG | GCA | TTG | GAG | CAT | GCT | CTC | AAG | TAC | AGT | TTG | 1424 |
| Cys | Val | Ala | Asp | Val | Glu | Ala | Leu | Glu | His | Ala | Leu | Lys | Tyr | Ser | Leu |  |
|  |  |  |  | 405 |  |  |  | 410 |  |  |  | 415 |  |  |  |
| CCT | GGC | TTG | ATT | CGT | CGA | TTG | TGG | TCG | AGT | AAG | CGT | CAG | TCG | GGC | GTA | 1472 |
| Pro | Gly | Leu | Ile | Arg | Arg | Leu | Trp | Ser | Ser | Lys | Arg | Gln | Ser | Gly | Val |  |
|  |  |  | 420 |  |  |  | 425 |  |  |  | 430 |  |  |  |  |
| TCG | CGC | GAG | ATT | GGC | GTT | GTG | GTG | GTA | GAC | AAT | CTT | CCA | GCG | CTT | TTC | 1520 |
| Ser | Arg | Glu | Ile | Gly | Val | Val | Val | Val | Asp | Asn | Leu | Pro | Ala | Leu | Phe |  |
|  |  | 435 |  |  |  | 440 |  |  |  | 445 |  |  |  |  |  |
| CAG | CAA | GAT | CAA | GCG | GCA | GCG | AGC | GAT | ATC | GAC | TCG | CTC | TTC | CAA | CGC | 1568 |
| Gln | Gln | Asp | Gln | Ala | Ala | Ala | Ser | Asp | Ile | Asp | Ser | Leu | Phe | Gln | Arg |  |
|  | 450 |  |  |  | 455 |  |  |  | 460 |  |  |  |  |  |  |
| TCA | AAG | ATG | CTA | GTC | GAG | ATC | GCG | GAT | GCG | CTC | AAG | CGT | ATC | AGT | GCT | 1616 |
| Ser | Lys | Met | Leu | Val | Glu | Ile | Ala | Asp | Ala | Leu | Lys | Arg | Ile | Ser | Ala |  |
| 465 |  |  |  | 470 |  |  |  | 475 |  |  |  |  |  |  | 480 |
| GTA | CAA | TGG | CGT | GGC | GCT | TCA | GAT | TGT | GGT | TCC | TCT | GCA | GGT | AGA | GCG | 1664 |
| Val | Gln | Trp | Arg | Gly | Ala | Ser | Asp | Cys | Gly | Ser | Ser | Ala | Gly | Arg | Ala |  |

-continued

|     |     |     | 485 |     |     |     | 490 |     |     |     |     | 495 |     |     |      |
|-----|-----|-----|-----|-----|-----|-----|-----|-----|-----|-----|-----|-----|-----|-----|------|
| GTG | CTG | GTG | CTG | AAC | CAC | GTC | AGC | GAT | GCG | TTT | GGA | ATC | GAC | AAG | CAG  | 1712 |
| Val | Leu | Val | Leu | Asn | His | Val | Ser | Asp | Ala | Phe | Gly | Ile | Asp | Lys | Gln  |
|     |     |     | 500 |     |     |     | 505 |     |     |     |     | 510 |     |     |      |

```
ATT  GCA  CGG  CGC  TTC  GTA  TTC  GAC  TCG  GCG  CAC  CGC  ATC  CGA  ACG  CGT      1760
Ile  Ala  Arg  Arg  Phe  Val  Phe  Asp  Ser  Ala  His  Arg  Ile  Arg  Thr  Arg
               515                 520                 525

CGG  TCT  CAT  TTT  GCA  CGC  AAC  GAT  CCT  GGC  ACA  TCA  AGT  CAA  GCG  CCA      1808
Arg  Ser  His  Phe  Ala  Arg  Asn  Asp  Pro  Gly  Thr  Ser  Ser  Gln  Ala  Pro
     530                      535                 540

ACC  TCG  GCA  TTC  AGC  GGT  GGC  ACT  GGA  TCG  GCG  TTA  CCC  GAC  CAG  CCG      1856
Thr  Ser  Ala  Phe  Ser  Gly  Gly  Thr  Gly  Ser  Ala  Leu  Pro  Asp  Gln  Pro
545                      550                 555                      560

CTA  GCG  ATG  GAT  GTG  GCT  AGC  CAG  ACT  GCG  TTC  ACC  AGC  GGG  CTG  CTC      1904
Leu  Ala  Met  Asp  Val  Ala  Ser  Gln  Thr  Ala  Phe  Thr  Ser  Gly  Leu  Leu
                    565                 570                      575

GCC  TCG  ATC  GCG  CCT  ACG  CTG  GCG  GAA  GCG  GTT  GGC  GCA  CGC  GAG  CTC      1952
Ala  Ser  Ile  Ala  Pro  Thr  Leu  Ala  Glu  Ala  Val  Gly  Ala  Arg  Glu  Leu
               580                 585                      590

GAC  TCG  GCG  TGC  GCT  TCC  AAC  GAT  GTG  CCG  CTC  CGC  ACA  CTT  GAA  GCA      2000
Asp  Ser  Ala  Cys  Ala  Ser  Asn  Asp  Val  Pro  Leu  Arg  Thr  Leu  Glu  Ala
          595                      600                 605

CGC  ACT  GCA  CAG  CTC  GGT  CAG  ACC  TGG  AGC  AAC  CTG  ATC  AAT  GTG  CGC      2048
Arg  Thr  Ala  Gln  Leu  Gly  Gln  Thr  Trp  Ser  Asn  Leu  Ile  Asn  Val  Arg
     610                      615                 620

GTG  TTT  CTG  TCC  AAA  ACG  CGC  GCC  AGG  ATA  TGC  ATG  CGC  GAC  GAT  CAG      2096
Val  Phe  Leu  Ser  Lys  Thr  Arg  Ala  Arg  Ile  Cys  Met  Arg  Asp  Asp  Gln
625                      630                 635                      640

GCA  CCA  GCA  TGC  GAG  CCA  GTG  CGC  CAA  AAC  ACC  AAT  CAA  CGT  GGT  ACG      2144
Ala  Pro  Ala  Cys  Glu  Pro  Val  Arg  Gln  Asn  Thr  Asn  Gln  Arg  Gly  Thr
                    645                 650                      655

GCG  AGC  AAG  TCG  CTC  ATG  AAT  ACG  GTG  CGC  AAA  GCG  GCG  GTG  GTC  ATC      2192
Ala  Ser  Lys  Ser  Leu  Met  Asn  Thr  Val  Arg  Lys  Ala  Ala  Val  Val  Ile
               660                 665                      670

AAT  CCA  TTT  GGC  GCA  ACC  ATG  TTA  GAC  GTC  GGC  GTC  GAC  AAG  AGC  GCG      2240
Asn  Pro  Phe  Gly  Ala  Thr  Met  Leu  Asp  Val  Gly  Val  Asp  Lys  Ser  Ala
          675                      680                 685

CTG  AGA  CAG  CTA  CGG  TTT  GTC  ATT  ACG  CCG  CGC  AAA  GCG  GTG  CAT  GTG      2288
Leu  Arg  Gln  Leu  Arg  Phe  Val  Ile  Thr  Pro  Arg  Lys  Ala  Val  His  Val
     690                      695                 700

CTG  AAT  GCG  TAT  CCA  TCG  ACA  GTG  ATG  CAT  GCC  ATG  CAT  GCG  ACC  GCT      2336
Leu  Asn  Ala  Tyr  Pro  Ser  Thr  Val  Met  His  Ala  Met  His  Ala  Thr  Ala
705                      710                 715                      720

GAC  AGC  ACG  CCC  GCT  CCA  GAG  TCA  CAG  CAG  CAA  CAG  CGC  GCA  GCA  GAG      2384
Asp  Ser  Thr  Pro  Ala  Pro  Glu  Ser  Gln  Gln  Gln  Gln  Arg  Ala  Ala  Glu
                    725                 730                      735

CGC  CAC  CCA  GCG  GAG  CAA  GAG  GAC  GCC  GAT  CAA  GAC  CTC  TTC  GGA  GAA      2432
Arg  His  Pro  Ala  Glu  Gln  Glu  Asp  Ala  Asp  Gln  Asp  Leu  Phe  Gly  Glu
               740                 745                      750

GCG  CTG  CAA  GAG  CAT  CAC  TGG  CTA  GCC  ATC  GAC  GAG  CTC  CAA  TCG  CAC      2480
Ala  Leu  Gln  Glu  His  His  Trp  Leu  Ala  Ile  Asp  Glu  Leu  Gln  Ser  His
     755                      760                 765

ACC  ACC  GCG  CGT  CCG  ACT  TCC  CGA  GCC  GCC  CAA  GCT  GGC  T GAGTGAAAGA       2530
Thr  Thr  Ala  Arg  Pro  Thr  Ser  Arg  Ala  Ala  Gln  Ala  Gly
770                      775                 780

TTGACTGAGT  CATCTCACGT  CTGCGATCCA  GAATCCTTCG  TATTTCTACA  CACATCACAG      2590

GATCGTGTTC  GTATTCGCGA  TCATATCGTA  CACAACTCAA  GTTATTGACG  TTGAAATGCA      2650

TTCGTGATTC  ACGCTTGTAG  CATGCTAGAC  GCGAGGCAAG  TCTCTTTGGC  GCTCATGTTT      2710
```

```
AAGCTGGCAC AGGCACGAGC GTCGATTCGG GAAAATGGAA AAAAGGAAGA ACGGCACCAA    2770

GATTGACTGT GTTTAAGTTG AGAGCAAATC GACAACAGTG AAGCATGCTA CAAGTTGTCG    2830

AGCTAGGCGC CGATCTGCGC GTCCCATGAT GCTCTCAGCT GCGGTTCGAC GGCGTTCCAG    2890

ATGTGCGACC ATGTGTCGTC GCCCACCTGT GCTCTGAATT GGTCGAGCGC GGATTTGAAC    2950

CAGACCTTGA CTTGTGCGCC GTGGAGGATG TGCTTGGTAG CGTCCGATTT GATCGTTTCG    3010

CTGGCGGCCA ATTTGGTGAA GCCGGTCTGG AAGCCTGCAG CATGGTCTTC GTCGGCGAAC    3070

AGCAGATCCA CGTCTTGCGT CTGCGTCGCC GAGCTGGGCG TGAGCAGCAA CCGCAACAGC    3130

GCTGCGAGCA ATGTTGGCAA CACGCTCACA TTCGGCGCTC GACGCATGGC CGATGAATTC    3190

ACCAACAAGC TCGCAA                                                    3206
```

( 2 ) INFORMATION FOR SEQ ID NO:2:

( i ) SEQUENCE CHARACTERISTICS:
        ( A ) LENGTH: 781 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Thr Gly Ile Ala Ile Ala Asp Val Gly Cys Ile Ser Lys Arg Ile
 1               5                  10                  15

Lys Ala Cys Cys Arg Arg Ala Lys Leu Phe Ser Thr Asp Glu Ile Leu
             20                  25                  30

Leu Ser Pro Pro Gln Gln Leu Ala His Val Leu Arg Ile Ser Gln Ala
         35                  40                  45

Asp Ala Asp Leu Leu Leu Leu Gln Val Ala Thr Ala Ser Ala Pro Pro
     50                  55                  60

Pro Ile Ser Val Leu Asp Ala Leu Asn Gly Lys Leu Pro Ala Thr Asn
 65                  70                  75                  80

Leu Asp Gln Asn Phe Phe Asp Ala Val Ala Ala Ala Asp Asp Asp Asp
                 85                  90                  95

Asp Asp Asn Asp Asp Asp Asp Lys Ala Asp Ser Gly Ser Ala Asp
             100                 105                 110

Ala Ser Asp Thr Ser Asp Ala Asp Gln His Leu Asn Asp Ala Arg
         115                 120                 125

Phe Ala Ser Ser Cys Ile Val Pro Pro Thr Gln Gly Tyr Asp Gly Asn
     130                 135                 140

Phe Pro Gly Ala Gln Cys Phe Val Tyr Asp Asp Ala Gly Ser Asp
 145                 150                 155             160

Ser Asp Ala Arg Ser Ser Ile Asp Ala Val Met His Glu Asp Ile Glu
                 165                 170                 175

Leu Pro Ser Thr Phe Cys Arg Pro Gln Thr Pro Gln Thr His Asp Val
             180                 185                 190

Ala Arg Asp Glu His His Asp Gly Tyr Leu Cys Asp Pro Lys Val Asp
         195                 200                 205

His Ala Ser Val Ala Arg Asp Val Leu Ser Leu Gly Arg Gln Arg His
     210                 215                 220

Val Phe Ser Ser Gly Ser Arg Glu Leu Asp Asp Leu Leu Gly Gly Gly
 225                 230                 235             240

Val Arg Ser Ala Val Leu Thr Glu Leu Val Gly Glu Ser Gly Ser Gly
                 245                 250                 255

Lys Thr Gln Met Ala Ile Gln Val Cys Thr Tyr Ala Ala Leu Gly Leu
             260                 265                 270
```

| Val | Pro | Leu | Ser | Gln | Ala | Asp | Asp | His | Asp | Lys | Gly | Asn | Asn | Thr | Phe |
|||||||||||||||||
|     |     | 275 |     |     |     |     | 280 |     |     |     |     | 285 |     |     |     |
| Gln | Ser | Arg | Thr | Phe | Val | Arg | Asp | Pro | Ile | His | Ala | Ser | Thr | Lys | Asp |
|     | 290 |     |     |     |     | 295 |     |     |     |     | 300 |     |     |     |     |
| Asp | Thr | Leu | Ser | Asp | Ile | Leu | Gln | Ser | Tyr | Gly | Met | Glu | Pro | Ser | Ile |
| 305 |     |     |     |     | 310 |     |     |     |     | 315 |     |     |     |     | 320 |
| Gly | Ser | His | Arg | Gly | Met | Gly | Ala | Cys | Tyr | Ile | Thr | Ser | Gly | Gly | Glu |
|     |     |     |     | 325 |     |     |     |     | 330 |     |     |     |     | 335 |     |
| Arg | Ala | Ala | His | Ser | Ile | Val | Asn | Arg | Ala | Leu | Glu | Leu | Ala | Ser | Phe |
|     |     |     | 340 |     |     |     |     | 345 |     |     |     |     | 350 |     |     |
| Ala | Ile | Asn | Glu | Arg | Phe | Asp | Arg | Val | Tyr | Pro | Val | Cys | Asp | Pro | Thr |
|     |     | 355 |     |     |     |     | 360 |     |     |     |     | 365 |     |     |     |
| Gln | Ser | Ser | Gln | Asp | Ala | Asp | Gly | Arg | Arg | Asp | Ala | Leu | Leu | Ala | Lys |
|     | 370 |     |     |     |     | 375 |     |     |     |     | 380 |     |     |     |     |
| Ala | Gln | Gln | Leu | Gly | Arg | Arg | Gln | Ala | Leu | Ala | Asn | Leu | His | Ile | Ala |
| 385 |     |     |     |     | 390 |     |     |     |     | 395 |     |     |     |     | 400 |
| Cys | Val | Ala | Asp | Val | Glu | Ala | Leu | Glu | His | Ala | Leu | Lys | Tyr | Ser | Leu |
|     |     |     |     | 405 |     |     |     |     | 410 |     |     |     |     | 415 |     |
| Pro | Gly | Leu | Ile | Arg | Arg | Leu | Trp | Ser | Ser | Lys | Arg | Gln | Ser | Gly | Val |
|     |     |     | 420 |     |     |     |     | 425 |     |     |     |     | 430 |     |     |
| Ser | Arg | Glu | Ile | Gly | Val | Val | Val | Asp | Asn | Leu | Pro | Ala | Leu | Phe |
|     |     | 435 |     |     |     |     | 440 |     |     |     |     | 445 |     |     |
| Gln | Gln | Asp | Gln | Ala | Ala | Ala | Ser | Asp | Ile | Asp | Ser | Leu | Phe | Gln | Arg |
|     | 450 |     |     |     |     | 455 |     |     |     |     | 460 |     |     |     |     |
| Ser | Lys | Met | Leu | Val | Glu | Ile | Ala | Asp | Ala | Leu | Lys | Arg | Ile | Ser | Ala |
| 465 |     |     |     |     | 470 |     |     |     |     | 475 |     |     |     |     | 480 |
| Val | Gln | Trp | Arg | Gly | Ala | Ser | Asp | Cys | Gly | Ser | Ser | Ala | Gly | Arg | Ala |
|     |     |     |     | 485 |     |     |     |     | 490 |     |     |     |     | 495 |     |
| Val | Leu | Val | Leu | Asn | His | Val | Ser | Asp | Ala | Phe | Gly | Ile | Asp | Lys | Gln |
|     |     |     |     | 500 |     |     |     |     | 505 |     |     |     |     | 510 |     |
| Ile | Ala | Arg | Arg | Phe | Val | Phe | Asp | Ser | Ala | His | Arg | Ile | Arg | Thr | Arg |
|     |     |     | 515 |     |     |     |     | 520 |     |     |     |     | 525 |     |     |
| Arg | Ser | His | Phe | Ala | Arg | Asn | Asp | Pro | Gly | Thr | Ser | Ser | Gln | Ala | Pro |
|     | 530 |     |     |     |     | 535 |     |     |     |     | 540 |     |     |     |     |
| Thr | Ser | Ala | Phe | Ser | Gly | Gly | Thr | Gly | Ser | Ala | Leu | Pro | Asp | Gln | Pro |
| 545 |     |     |     |     | 550 |     |     |     |     | 555 |     |     |     |     | 560 |
| Leu | Ala | Met | Asp | Val | Ala | Ser | Gln | Thr | Ala | Phe | Thr | Ser | Gly | Leu | Leu |
|     |     |     |     | 565 |     |     |     |     | 570 |     |     |     |     | 575 |     |
| Ala | Ser | Ile | Ala | Pro | Thr | Leu | Ala | Glu | Ala | Val | Gly | Ala | Arg | Glu | Leu |
|     |     |     | 580 |     |     |     |     | 585 |     |     |     |     | 590 |     |     |
| Asp | Ser | Ala | Cys | Ala | Ser | Asn | Asp | Val | Pro | Leu | Arg | Thr | Leu | Glu | Ala |
|     |     | 595 |     |     |     |     | 600 |     |     |     |     | 605 |     |     |     |
| Arg | Thr | Ala | Gln | Leu | Gly | Gln | Thr | Trp | Ser | Asn | Leu | Ile | Asn | Val | Arg |
|     | 610 |     |     |     |     | 615 |     |     |     |     | 620 |     |     |     |     |
| Val | Phe | Leu | Ser | Lys | Thr | Arg | Ala | Arg | Ile | Cys | Met | Arg | Asp | Asp | Gln |
| 625 |     |     |     |     | 630 |     |     |     |     | 635 |     |     |     |     | 640 |
| Ala | Pro | Ala | Cys | Glu | Pro | Val | Arg | Gln | Asn | Thr | Asn | Gln | Arg | Gly | Thr |
|     |     |     |     | 645 |     |     |     |     | 650 |     |     |     |     | 655 |     |
| Ala | Ser | Lys | Ser | Leu | Met | Asn | Thr | Val | Arg | Lys | Ala | Ala | Val | Val | Ile |
|     |     |     | 660 |     |     |     |     | 665 |     |     |     |     | 670 |     |     |
| Asn | Pro | Phe | Gly | Ala | Thr | Met | Leu | Asp | Val | Gly | Val | Asp | Lys | Ser | Ala |
|     |     | 675 |     |     |     |     | 680 |     |     |     |     | 685 |     |     |     |
| Leu | Arg | Gln | Leu | Arg | Phe | Val | Ile | Thr | Pro | Arg | Lys | Ala | Val | His | Val |

|     |     |     |     |     | 690 |     |     |     |     | 695 |     |     |     |     | 700 |     |     |     |     |
|---|---|---|---|---|---|---|---|---|---|---|---|---|---|---|---|---|---|---|---|

Leu Asn Ala Tyr Pro Ser Thr Val Met His Ala Met His Ala Thr Ala
705                     710                 715                 720

Asp Ser Thr Pro Ala Pro Glu Ser Gln Gln Gln Gln Arg Ala Ala Glu
            725                 730                 735

Arg His Pro Ala Glu Gln Glu Asp Ala Asp Gln Asp Leu Phe Gly Glu
            740                 745                 750

Ala Leu Gln Glu His His Trp Leu Ala Ile Asp Glu Leu Gln Ser His
        755                 760                 765

Thr Thr Ala Arg Pro Thr Ser Arg Ala Ala Gln Ala Gly
770                 775                 780

( 2 ) INFORMATION FOR SEQ ID NO:3:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:3:

Met Gly Ser Ser His His His His His His Ser Ser Gly Leu Val Pro
1               5                   10                  15

Arg Gly Ser His
            20

( 2 ) INFORMATION FOR SEQ ID NO:4:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: unknown ( i i ) MOLECULE TYPE: DNA ( x i ) SEQUENCE DESCRIPTION: SEQ ID NO:4:

TAGAGGATCC CCGGGTTTTC CCGGGGATCC TCTAGAGTTT TTCTC          45

( 2 ) INFORMATION FOR SEQ ID NO:5:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: unknown ( i i ) MOLECULE TYPE: DNA/RNA ( i x ) FEATURE:
        ( A ) NAME/KEY: -
        ( B ) LOCATION: 20..34
        ( D ) OTHER INFORMATION: /label=a
          / note= ""RNA""

( x i ) SEQUENCE DESCRIPTION: SEQ ID NO:5:

TAGAGGATCC CCGGGTTTTC CCGGGGAUCC UCUAGAGTTT TCTC          44

( 2 ) INFORMATION FOR SEQ ID NO:6:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: unknown (  i i  ) MOLECULE TYPE: DNA (  x i  ) SEQUENCE DESCRIPTION: SEQ ID NO:6:

TTACGAATTC GAGCTCGGTA CCCGGGGATC CTCTAGAGTC GACCTGCAGG CATGCAAGCT　60

TGGCACTGGC CG　72

( 2 ) INFORMATION FOR SEQ ID NO:7:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: unknown ( i i ) MOLECULE TYPE: DNA ( x i ) SEQUENCE DESCRIPTION: SEQ ID NO:7:

CGGCCAGTGC CAAGCTTGCA TGCCTGCAGG TCGACTCTAG AGGATCCCCG GGTACCGAGC　60

TCGAATTCGT AA　72

( 2 ) INFORMATION FOR SEQ ID NO:8:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: unknown ( i i ) MOLECULE TYPE: DNA ( x i ) SEQUENCE DESCRIPTION: SEQ ID NO:8:

TTACGAATTC GAGCTCGGTA CCCGGGGATC CTCTAGAGTC GACCTGCAGG　50

( 2 ) INFORMATION FOR SEQ ID NO:9:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: unknown ( i i ) MOLECULE TYPE: DNA ( x i ) SEQUENCE DESCRIPTION: SEQ ID NO:9:

CCTGCAGGTC GACTCTAGAG GATCCCCGGG TACCGAGCTC GAATTCGTAA　50

( 2 ) INFORMATION FOR SEQ ID NO:10:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: unknown ( i i ) MOLECULE TYPE: DNA ( x i ) SEQUENCE DESCRIPTION: SEQ ID NO:10:

TTACGAATTC GAGCTCGGTA CCCGGGGATC　30

( 2 ) INFORMATION FOR SEQ ID NO:11:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: unknown ( i i ) MOLECULE TYPE: DNA ( x i ) SEQUENCE DESCRIPTION: SEQ ID NO:11:

GATCCCCGGG TACCGAGCTC GAATTCGTAA                                30

( 2 ) INFORMATION FOR SEQ ID NO:12:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: unknown ( i i ) MOLECULE TYPE: RNA ( x i ) SEQUENCE DESCRIPTION: SEQ ID NO:12:

GAUCCCCGGG UACCGAGCUC GAAUUCGUAA                                30

( 2 ) INFORMATION FOR SEQ ID NO:13:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: unknown ( i i ) MOLECULE TYPE: DNA ( x i ) SEQUENCE DESCRIPTION: SEQ ID NO:13:

ACAGCACCAG ATTCAGCAAT TAAGCTCTAA GCC                            33

( 2 ) INFORMATION FOR SEQ ID NO:14:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: unknown ( i i ) MOLECULE TYPE: DNA ( x i ) SEQUENCE DESCRIPTION: SEQ ID NO:14:

GAATTCGAGC TCGGTACCCG GGGATCCTCT AGAGTCGACC TGCA                44

( 2 ) INFORMATION FOR SEQ ID NO:15:

( i ) SEQUENCE CHARACTERISTICS:
        ( A ) LENGTH: 4 amino
        ( B ) TYPE: amino acid
        ( C ) TOPOLOGY: unknown ( i i ) MOLECULE TYPE: peptide ( i x ) FEATURE:
        ( A ) NAME/KEY: -
        ( B ) LOCATION: 1
        ( D ) OTHER INFORMATION: Xaa is Ser or Thr
        ( A ) NAME/KEY: -
        ( B ) LOCATION: 4
        ( D ) OTHER INFORMATION: Xaa is Arg or Lys ( x i ) SEQUENCE DESCRIPTION: SEQ ID NO:15:

Xaa Pro Xaa Xaa
1